(12) United States Patent
Wengel

(10) Patent No.: US 7,084,125 B2
(45) Date of Patent: *Aug. 1, 2006

(54) XYLO-LNA ANALOGUES

(75) Inventor: Jesper Wengel, Odense S (DK)

(73) Assignee: ExiQon A/S, Vedbaek (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 747 days.

This patent is subject to a terminal disclaimer.

(21) Appl. No.: 09/528,110

(22) Filed: Mar. 17, 2000

(65) Prior Publication Data

US 2003/0082807 A1    May 1, 2003

Related U.S. Application Data

(60) Provisional application No. 60/158,514, filed on Oct. 8, 1999, provisional application No. 60/127,359, filed on Apr. 1, 1999.

(30) Foreign Application Priority Data

Mar. 18, 1999  (DK) ................. PA 1999 00382
Sep. 1, 1999   (DK) ................. PA 1999 01224

(51) Int. Cl.
  *A61K 31/70*   (2006.01)
  *C07H 21/00*   (2006.01)
  *C07H 21/04*   (2006.01)

(52) U.S. Cl. ............... 514/44; 536/22.1; 536/23.1; 536/24.3; 536/24.5

(58) Field of Classification Search ........... 536/22.1, 536/24.5, 23.1, 25.34; 514/44; 435/91.5
See application file for complete search history.

(56) References Cited

U.S. PATENT DOCUMENTS

| | | | |
|---|---|---|---|
| 6,013,639 A * | 1/2000 | Peyman et al. ............... 514/44 |
| 6,268,490 B1 | 7/2001 | Imanishi et al. |
| 6,316,612 B1 * | 11/2001 | Matulic-Adamic et al. ............... 536/24.5 |
| 6,525,191 B1 | 2/2003 | Ramasamy |
| 2002/0068708 A1 * | 6/2002 | Wengel et al. ............... 514/44 |
| 2003/0018186 A1 | 1/2003 | Ramasamy et al. |

FOREIGN PATENT DOCUMENTS

| EP | 0538194 B1 | 4/1999 |
|---|---|---|
| WO | WO98/22489 | 5/1998 |
| WO | WO98/39352 | 9/1998 |
| WO | WO 99/60855 | 2/1999 |
| WO | WO99/14226 | 3/1999 |

OTHER PUBLICATIONS

Norrild et al. A highly stereoselective synthesis of 1-amino-2,5-anhydro-1-deoxyhexitois via 2-trifluoromethyl-oxazolinium intermediates. Carbohydrate Research, vol. 297, pp. 261-272, 1997.*
Stanley Crooke, Antisense Research and Applications, Chapter 1, Basic Principles of Antisense Therapeutics, Jul. 1998, Springer-Verlag Press, Berlin, Heidelberg, New York, pp. 1-50.*
Tarkoy et al., *Helv. Chim. Acta*, 76:481 (1993), pp. 481-510.
Tarkoy et al., *Angew. Chem., Int. Ed. Engl.*, 32:1432 (1993), vol. 32, No. 10 pp. 1432-1434.
Egli et al., *J. Am. Chem. Soc.*, 115:5855 (1993), pp. 5855-5856.
Tarkoy et al., *Helv. Chim. Acta*, 77:716 (1994), pp. 716-744.
Bolli et al., *Angew. Chem., Int. Ed. Engl.*, 34:694 (1995), vol. 34, No. 6, pp. 694-696.
Bolli et al., *Helv. Chim. Acta*, 78:2077 (1995), pp. 2077-2096.
Litten et al., *Bioorg. Med. Chem. Lett.*, 5:1231 (1995), pp. 1231-1234.
Litten et al., *Helv. Chim. Acta*, 79:1129 (1996), pp. 1129-1146.

(Continued)

*Primary Examiner*—Janet Epps Ford
(74) *Attorney, Agent, or Firm*—Peter F. Corless; Stephana E. Patton; Edwards, Angell, Palmer & Dodge LLP

(57) ABSTRACT

Based on the above and on the remarkable properties of the 2'-O,4'-C-methylene bridged LNA monomers it was decided to synthesise oligonucleotides comprising one or more 2'-O, 4'-C-methylene-β-D-xylofuranosyl nucleotide monomer(s) as the first stereoisomer of LNA modified oligonucleotides. Modelling clearly indicated the xylo-LNA monomers to be locked in an N-type furanose conformation. Whereas the parent 2'-deoxy-β-D-xylofuranosyl nucleosides were shown to adopt mainly an N-type furanose conformation, the furanose ring of the 2'-deoxy-β-D-xylofuranosyl monomers present in xylo-DNA were shown by conformational analysis and computer modelling to prefer an S-type conformation thereby minimising steric repulsion between the nucleobase and the 3'-O-phopshate group (Seela, F.; Wömer, Rosemeyer, H. *Helv. Chem. Acta* 1994, 77, 883). As no report on the hybridisation properties and binding mode of xylo-configurated oligonucleotides in an RNA context was believed to exist, it was the aim to synthesise 2'-O,4'-C-methylene-β-D-xylofuranosyl nucleotide monomer and to study the thermal stability of oligonucleotides comprising this monomer. The results showed that fully modified or almost fully modified Xylo-LNA is useful for high-affinity targeting of complementary nucleic acids. When taking into consideration the inverted stereochemistry at C-3' this is a surprising fact. It is likely that Xylo-LNA monomers, in a sequence context of Xylo-DNA monomers, should have an affinity-increasing effect.

41 Claims, 2 Drawing Sheets

OTHER PUBLICATIONS

Figure 1:
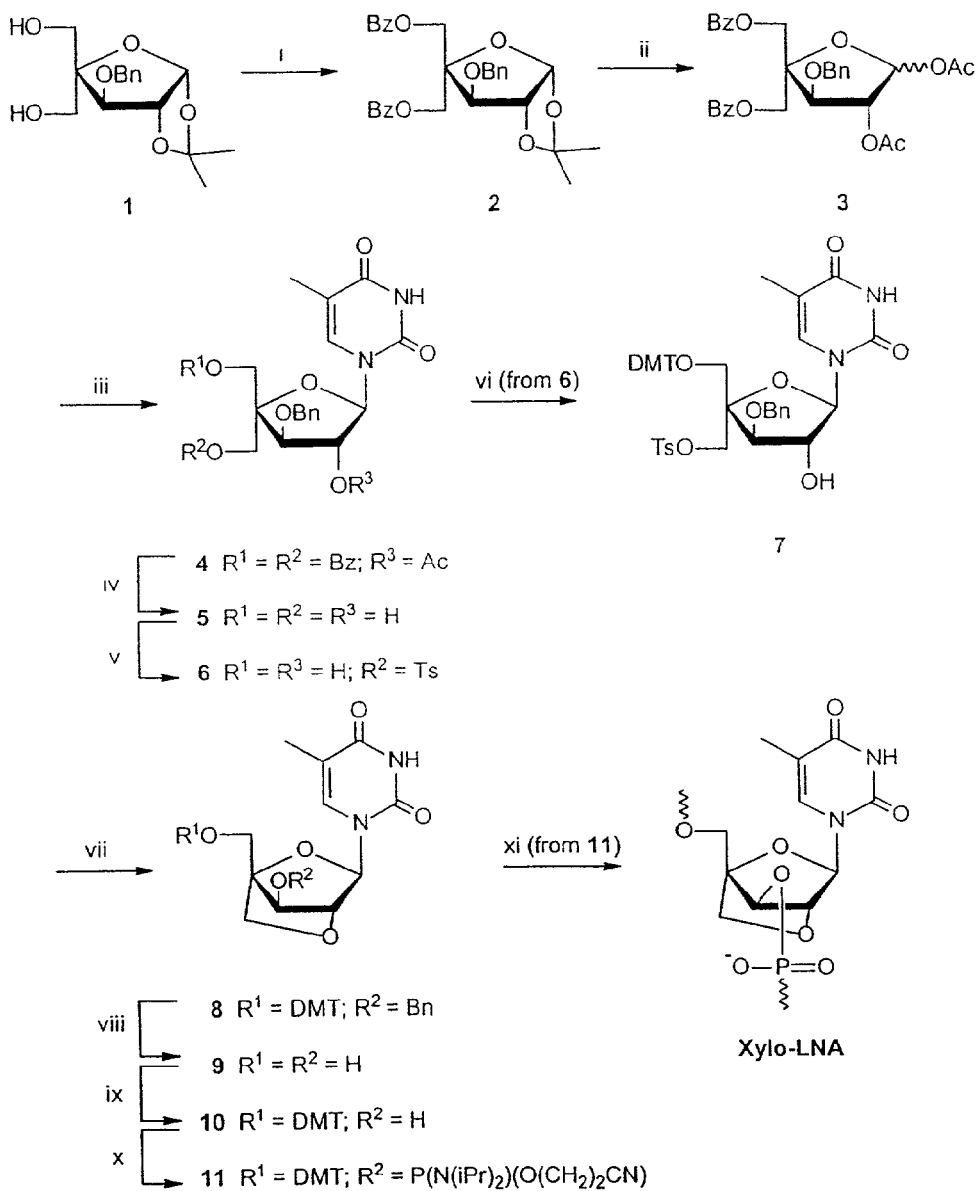

Bolli et al., *Chem. Biol.*, 3:197 (1996), pp. 197-205.
Bolli et al., *Nucleic Acids. Res.*, 24:4660 (1996), pp. 4660-4667.
K.H. Altmann et al., *Tetrahedron Lett.*, 35::2331 (1994), pp. 2331-2334.
K. H. Altmann et al., *Tetrahedron Lett.*, 35:7625 (1994), pp. 7625-7628.
Marquez et al., *J. Med. Chem.*, 39:3739 (1996), pp. 3739-3747.
Ezzitouni et al., *J. Chem. Soc., Perkin Trans.*, 1:1073 (1997), pp. 1073-1078.
Jones et al., *J. Am. Chem. Soc.*, 115:9816 (1993), pp. 9816-9817.
Wang et al., *Bioorg. Med. Chem. Lett.*, 7: 229 (1997), pp. 229-232.
Yannopoulus et al., *Synlett*, 378 (1997), pp. 378-380.
Chima, 36th IUPAC Congress, organized by the Swiss Chemical Society. Poster No. SB-B4: Steffens, R. and Leumann Ch. Tricyclo-DNA: synthesis, enzymatic stability, and pairing properties.
Nielsen, Master Thesis (Odense University, Denmark), p. 67-71 (1995).
Youssefyeh et al., *J. Org. Chem.*, 44:1301 (1979), pp. 1301-1308.
Jones et al., *J. Org. Chem.*, 44:1309 (1979), pp. 1309-1317.
Yang et al., *Tetrahedron Lett.*, 33:37 (1992), pp. 37-40.
Thrane et al., *Tetrahedron*, 51:10389 (1995), pp. 10389-10402.
Nielsen et al., *Bioorg. Med. Chem.*, 3:1493 (1995), pp. 1493-1502.
Freier et al., *Nucleic Acid Research*, 25:4429-4443 (1997).
Haly et al., *SYNLETT*, 687-689 (1996).
Zou et al., *Tetrahedron Lett.*, 37:941-944 (1996).
Herdewijn., *Liebigs Ann.*, 1337-1348 (1996).
Obika et al., *Tetrahedron Lett.*, 39:5401-5404 (1998).
Obika et al., *Tetrahedron Lett.*, 38:8735-8738 (1997).
7th Antisense Symposium, Nov. 21-22, 1997. Poster No. 32 and 33: Obika, D.N.; Morio, K. and Imanishi, T. Synthesis and properties of oligonucleotides containing novel bicyclic nucleosides with a fixed N-form sugar puckering.
Chima, 36th IUPAC Congress, organized by the Swiss Chemical Society. Poster No. SB-B12: Egtger, A. and Leumann Ch. Designe, synthesis and properties of bicyclo [3.2.1]-amio nucleic acids.
Chima, 36th IUPAC Congress, organized by the Swiss Chemical Society. Poster No. SB-B5: Epple, C. Ch., Pompizi, I. and Leumann Ch. Bicyclo [3.2.1]-DNA: an oligonucleotide analogue with a conformationally preorganized Phosphodiester backbone and a flexible sugar-base linkage.
Sep. 6-10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'-Deoxy-2'-C, 4'-C-Bridged Bicyclic Nucleoside".
Sep. 6-10, 1998: 13th International Round Table—Nucleoside, Nucleotides and their Biological Applications, Montpeilleir: Poster No. 288: Meldgaard, M. et al., "LNA (Locked Nucleic Acids): Synthesis and Thermal Denaturation Studies".
Sep. 6-10, 1998: 13th International Round Table—Nucleoside, Nucleotides and their Biological Applications, Montpeilleir: Poster No. 287 and Proceeding:
Koshkin, A. A. et al., "Locked Nucleic Acids as synthetic RNA Mimics for Effective Complementary Recognition."
Sep. 6-10, 1998: 13th International Round Table—Nucleoside, Nucleotides and their Biological Applications, Montpeilleir: Poster No. 67: Nielsen, P. and Wengel, J. "A New Convergent Synthetic Approach Towards a-and β-LNA (Locked Nucleic Acids)".
Oct. 8, 1998: Antisense 98, Targeting the Molecularl Basis of Disease: Poster No. 24: Havsteen, M. et al., "LNA (Locked Nucleic Acids): A new Class of High Affinity Nucleic Acids With Prime Potential as Antisense and Antigene Agents".
Jan. 21, 1998: National Seminar on Perspectives in Interfacial Areas of Chemistry and Biology, Delhi University: Wengel, J. "LNA (Locked Nucleic Acids): Synthesis and High Affinity Nucleic Acid Recognition—Stop the Twisting."
27 Marts 1998: Workshop of Young European Bioorganic Chemists, Munchen: Wengel, J. "LNA (Locked Nucleic Acids): Synthesis and High Affinity Nucleic Acid Recognition—Stop the Twisting."
Aug. 20, 1998: Årsmødet for Center for Medicinsk Biotecknologi, KVL: Wengel, J. "LNA (Locked Nucleic Acids)"ations, Montpeilleir: Oral Communication 1: Wang, G. and Gunic, E. "Conformationally Locked Nucleoside Analogs. Synthesis of 2'-Deoxy-2'-C, 4'-C-Bridged Bicyclic Nucleoside".
Sep. 7, 1998: 13th International Round Table—Nucleoside, Nucleotides and their Biological Applications, Montpeilleir: Oral Communication 2: Wengel, J "LNA (locked Nucleic Acids)".
Sep. 8, 1998: Meeting in Lund, Sweden: Jakobsen, M. H. "LNA (Locked Nucleic Acids): A new Class of High Affinity Nucleic Acids With Prime Potential as Antisense and Antigene Agents".
Nielsen et al., *J. Chem. Soc., Perkin Trans.*, 1:3423-3433 (1997).
Nielsen et al., *Chem. Commun.*, 9:825-826 (1997).
Singh et al., *Chem. Commun.*, 455-456 (1998).
Koshkin et al., *Tetrahedron* , 54:36073630 (1998).
Koshkin et al., *Tetrahedron Lett.*, 39:4381-8384 (1998).
Singh et al., *Chem. Commun.*, 1237-1248 (1998).
Singh et al., *J. Org. Chem.*, 63:6078-6079 (1998).
Christensen et al., *J. Am. Chem. Soc.*, 120:5458-5463 (1998).
Koshkin et al., *J. Org. Chem.*, 63:2778-2781 (1998).
Kumar et al., *Bioorg. Med. Chem. Lett.*, 8:2219-2222 (1998).
Wengel et al., *Acc. Chem. Res.*, 32:301-310 (1999).
Koshkin et al., *J. Am. Chem. Soc.*, 120:13252-13253 (1998).
Nielsen et al., *Chem. Commun.*, 2645-2646 (1998).
Wengel et al., *Nucleosides Nucleoties*, 18:1365-1370 (1999).
Nielsen et al., *Nucleosides Nucleotides*, 18:701-702 (1999).
Kæmo et al., *Chem. Commun.*, 657-658 (1999).
Rajwanshi et al., *J. Chem. Soc., Perkin Trans.*, 1:1407-1414 (1999).
Raunkjaer et al., *J. Chem. Soc., Perkin Trans.*, 1:2543-2551 (1999).
Rajwanshi et al., *Chem. Commun.*, 1395-1396 (1999).
Pfundheller et al., *Nucleosides Nucleotides*, 18:2017-2030 (1999).
Rajwanshi et al., *Chem. Commun.*, 2073-2074 (1999).
Nielsen et al., *J. Biomol. Struc. Dyn.*, 17:175-191 (1999).
Nielsen et al., *Bioconjugate Chem.*, 11:228-238 (2000).
Rajwanshi et al., *Angewandte Chemie*, 39:1656-1659 (2000).

Minasov et al., *Biochemistry*, 39:3525 (2000).
Wahlesttedt et al., *Proc. Natl. Acad. Sci. USA*, 97:5633-5638 (2000).
Obika et al., *Tetrahedron Lett.*, 40:6465-6468 (1999).
Obika et al., *Tetrahedron Lett.*, 41:215-219 (1999).
Obika et al., *J. Chem. Soc., Chem. Commun.*, 2423-2424 (1999).
Wang et al., *Bioorg. Med. Chem. Lett.*, 9:1147-1150 (1999).
Obika et al., *Tetrahedron Lett.*, 41:221-224 (1999).
Obika et al., *Bioorg. Med. Chem. Lett.*, 9:515-518 (1999).
Obika et al., *Tetrahedron Lett.*, 39:5401-5405 (1998).

Imanishi et al., *J. Synth. Org. Chem.*, 57:959-980 (1999).
Chemical Abstracts, vol. 70, No. 1, Abstract No. 3737B (1969).
*Monatsch. Chem.*, 99(5):2111-2120 (1968).
Imanishi, T., et al. "Synthesis And Property Of Novel Conformationally Constrained Nucleoside And Oligonucleotide Analogs", The Sixteenth International Congress Of Heterocyclic Chemistry, Aug. 10-15, 1997, four pages.

* cited by examiner

XYLO-LNA ANALOGUES

This application claims the benefit of U.S. Provisional Application No. 60/127,359 filed Apr. 1, 1999 and U.S. Provisional Application No. 60/158,514 filed Oct. 8, 1999.

FIELD OF THE INVENTION

The present invention relates to the field of xylo-configurated bicyclic nucleoside analogues and to the synthesis of such nucleoside analogues which are useful in the formation of synthetic oligonucleotides capable of forming nucleobase specific duplexes with complementary single stranded and double stranded nucleic acids. The invention also relates to the field of xylo-configurated bicyclic nucleoside analogues which may be used as therapeutic drugs and which may be incorporated in oligonucleotides.

BACKGROUND OF THE INVENTION

Synthetic oligonucleotides are widely used compounds in disparate fields such as molecular biology and DNA-based diagnostics and therapeutics.

General Considerations

To be useful in the extensive range of the different applications outlined above oligonucleotides have to satisfy a large number of different requirements. As therapeutics, for instance, a useful oligonucleotide must be able to penetrate the cell membrane, have good resistance to extra- and intracellular nucleases and preferably have the ability to recruit endogenous enzymes like RNAseH. In DNA-based diagnostics and molecular biology other properties are important such as, e.g., the ability of oligonucleotides to act as efficient substrates for a wide range of different enzymes evolved to act on natural nucleic acids, such as e.g. polymerases, kinases, ligases and phosphatases. The fundamental property of oligonucleotides, however, which underlies all uses is their ability to recognise and hybridise sequence specifically to complementary single stranded nucleic acids employing either Watson-Crick hydrogen bonding (A—T and G—C) or other hydrogen bonding schemes such as the Hoogsteen mode. The two important terms, affinity and specificity, are commonly used to characterise the hybridisation properties of a given oligonucleotide. Affinity is a measure of the binding strength of the oligonucleotide to its complementary target sequence (expressed as the thermostability ($T_m$) of the duplex). Each nucleobase pair in the duplex adds to the thermostability and thus affinity increases with increasing size (number of nucleobases) of the oligonucleotide. Specificity is a measure of the ability of the oligonucleotide to discriminate between a fully complementary and a mismatched target sequence. In other words, specificity is a measure of the loss of affinity associated with mismatched nucleobase pairs in the target.

At constant oligonucleotide size, the specificity increases with increasing number of mismatches between the oligonucleotide and its targets (i.e. the percentage of mismatches increases). Conversely, specificity decreases when the size of the oligonucleotide is increased at a constant number of mismatches (i.e. the percentage of mismatches decreases). Stated another way, an increase in the affinity of an oligonucleotide occurs at the expense of specificity and vice-versa.

Given the shortcomings of natural oligonucleotides, new approaches for enhancing specificity and affinity are highly desirable for DNA-based therapeutics, diagnostics and for molecular biology techniques in general.

Conformationally Restricted Nucleosides

It is known that oligonucleotides undergo a conformational transition in the course of hybridising to a target sequence, from the relatively random coil structure of the single stranded state to the ordered structure of the duplex state.

Thus, conformational restriction has in recent years been applied to oligonucleotides in the search for analogues displaying improved hybridisation properties compared to the unmodified (2'-deoxy)oligonucleotides. For example bicyclo[3.3.0]nucleosides with an additional C-3',C-5'-ethano-bridge (M. Tarköy, M. Bolli, B. Schweizer and C. Leumann, *Helv. Chem. Acta*, 1993, 76, 481; Tarköy and C. Leumann, *Angew. Chem., Int. Ed. Engl.*, 1993, 32, 1432; M. Egli, P. Lubini, M. Dobler and C. Leumann, *J. Am. Chem. Soc.*, 1993, 115, 5855; M. Tarköy, M. Bolli and C. Leumann, *Helv. Chem. Acta*, 1994, 77, 716; M. Bolli 30 and C. Leumann, *Angew. Chem., Int. Ed. Engl.*, 1995, 34, 694; M. Bolli, P. Lubini and C. Leumann, *Helv. Chem. Acta*, 1995, 78, 2077; J. C. Litten, C. Epple and C. Leumann, *Bioorg. Med. Chem. Lett.*, 1995, 5, 1231; J. C. Litten and C. Leumann, *Helv. Chem. Acta*, 1996, 79, 1129; M. Bolli, J. C. Litten, R. Schultz and C. Leumann, *Chem. Biol.*, 1996, 3, 197; M. Bolli, H. U. Trafelet and C. Leumann, *Nucleic Acids Res.*, 1996, 24, 4660), bicarbocyclo[3.1.0]nucleosides with an additional C-1',C-6'- or C-6',C-4'-methano-bridge (K.-H. Altmann, R. Kesselring, E. Francotte and G. Rihs, *Tetrahedron Lett.*, 1994, 35, 2331; K.-H. Altmann, R. Imwinkelried, R. Kesselring and G. Rihs, *Tetrahedron Lett.*, 1994, 35, 7625; V. E. Marquez, M. A. Siddiqui, A. Ezzitouni, P. Russ, J. Wang, R. W. Wagner and M. D. Matteucci, *J. Med. Chem.*, 1996, 39, 3739; A. Ezzitouni and V. E. Marquez, *J. Chem. Soc., Perkin Trans.* 1, 1997, 1073), bicyclo[3.3.0]- and [4.3.0]nucleosides containing an additional C-2',C-3'-dioxalane ring synthesised as a dimer with an unmodified nucleoside where the additional ring is part of the internucleoside linkage replacing a natural phosphodiester linkage (R. J. Jones, S. Swaminathan, J. F. Millagan, S. Wadwani, B. S. Froehler and M. Matteucci, *J. Am. Chem. Soc.*, 1993, 115, 9816; J. Wang and M. D. Matteucci, *Bioorg. Med. Chem. Lett.*, 1997, 7, 229), dimers containing a bicyclo [3.1.0]nucleoside with a C-2',C-3'-methano bridge as part of amide- and sulfonamide-type internucleoside linkages (C. G. Yannopoulus, W. Q. Zhou, P. Nower, D. Peoch, Y. S. Sanghvi and G. Just, *Synlett*, 1997, 378), bicyclo[3.3.0] glucose-derived nucleoside analogue incorporated in the middle of a trimer through formacetal internucleoside linkages (C. G. Yannopoulus, W. Q. Zhou, P. Nower, D. Peoch, Y. S. Sanghvi and G. Just, *Synlett*, 1997, 378) and bicyclic [4.3.0]- and [3.3.0]nucleosides with additional C-2',C-3'-connected six- and five-membered ring (P. Nielsen, H. M. Pfundheller, J. Wengel, *Chem. Commun.*, 1997, 826; P. Nielsen, H. M. Pfundheller, J. Wengel, *XII International Roundtable: Nucleosides, Nucleotides and Their Biological Applications; La Jolla, Calif., Sep. 15–19, 1996*; Poster PPI 43) have been synthesised and incorporated into oligodeoxynucleotides. Unfortunately, oligonucleotides comprising these analogues form, in most cases, less stable duplexes with complementary nucleic acids compared to the unmodified oligonucleotides. In cases where a moderate improvement in duplex stability is observed, this relates only to either a DNA or an RNA target, or it relates to fully but not partly modified oligonucleotides or vice versa.

An appraisal of most of the reported analogues is further complicated by the lack of data on analogues with G, A and C nucleobases and lack of data indicating the specificity and mode of hybridisation. In many cases, synthesis of the reported monomer analogues is very complex while in other cases the synthesis of fully modified oligonucleotides is incompatible with the widely used standard phosphoramidite chemistry.

Recently, oligomers comprising Locked Nucleic Acids (LNA) have been reported (Nielsen, P., Pfundheller, H. M., Olsen, C. E. and Wengel, J., *J. Chem. Soc., Perkin Trans.* 1, 1997, 3423; Nielsen, P., Pfundheller, H. M., Wengel, J., *Chem. Commun.*, 1997, 9, 825; Christensen, N. K., Petersen, M., Nielsen, P., Jacobsen, J. P. and Wengel, J., *J. Am. Chem. Soc.,* 1998, 120, 5458; Koshkin, A. A. and Wengel, J., *J. Org. Chem.*, 1998, 63, 2778; Obika, S., Morio, K.-I., Hari, Y. and Imanishi, T., *Bioorg. Med. Chem. Lett.*, 1999, 515). Interestingly, incorporation of LNA monomers containing a 2'-O,4'-C-methylene bridge into an oligonucleotide sequence led to unprecedented improvement in the hybridisation ability of the modified oligonucleotide (Singh, S. K., Nielsen, P., Koshkin, A. A., Olsen, C. E. and Wengel, J., *Chem. Commun.*, 1998, 455; Koshkin, A. K., Singh, S. K., Nielsen, P., Rajwanshi, V. K., Kumar, R., Meldgaard, M., Olsen, C. E., and Wengel, J., *Tetrahedron*, 1998, 54, 3607; Koshkin, A. A. Rajwanshi, V. K., and Wengel, J., *Tetrahedron Lett.*, 1998, 39, 4381; Singh, Sanjay K. and Wengel, J., *Chem. Commun.*, 1998, 1247; Kumar, R., Singh, S. K., Koshkin, A. A., Rajwanshi, V. K., Meldgaard, M., and Wengel, J., *Bioorg. Med. Chem. Lett.*, 1998, 8, 2219; Obika, S. et al. *Tetrahedron Lett.*, 1997, 38, 8735; Obika, S. et al. *Tetrahedron Lett.*, 1998, 39, 5401; Singh, S. K., Kumar, R., and Wengel, J., *J. Org. Chem.*, 1998, 63, 6078; Koshkin, A. A., Nielsen, P., Meldgaard, M., Rajwanshi, V. K., Singh, S. K., and Wengel, J., *J. Am. Chem. Soc.*, 1998, 120, 13252; Singh, S. K., Kumar, R., and Wengel, J., *J. Org. Chem.*, 1998, 63, 10035). Oligonucleotides comprising these LNA monomers and the corresponding 2'-thio-LNA analogue form duplexes with complementary DNA and RNA with thermal stabilities not previously observed for bi- or tricyclic nucleosides modified oligonucleotides ($\Delta T_m$/modification=+3 to +11° C.) and show improved selectivity. In a series of papers, Seela et al. have studied xylo-DNA (FIG. 1, Base=adenin-9-yl, cytosin-1-yl, guanin-9-yl or thymin-1-yl) comprising one or more 2'-deoxy-β-D-xylofuranosyl nucleotide monomers (Rosemeyer, H.; Seela, F. *Helv. Chem. Acta* 1991, 74, 748; Rosemeyer, H.; Krecmerova, M.; Seela, F. *Helv. Chem. Acta* 1991 74, 2054; Seela, F.; Wörner, Rosemeyer, H. *Helv. Chem. Acta* 1994, 77, 883; Seela, F.; Heckel, M.; Rosemeyer, H. *Helv. Chem. Acta* 1996, 79, 1451; Rosemeyer, H.; Seela, F. *Nucleosides Nucleotides*, 1995, 14, 1041; Schoeppe, A.; Hinz, H.-J.; Rosemeyer, H.; Seela, F. *Eur. J. Biochem.* 1996, 239, 33). Compared with the corresponding natural 2'-deoxy-β-D-ribofuranosyl oligonucleotides, xylo-DNA generally display a mirror-image-like secondary structure, entropically favourable duplex formation, increased stability towards exonucleases, and, for oligonucleotides comprising a small number of 2'-deoxy-β-D-xylofuranosyl monomers, decreased thermal affinity towards complementary DNA (Rosemeyer, H.; Seela, F. *Helv. Chem. Acta* 1991, 74, 748; Rosemeyer, H.; Krecmerova, M.; Seela, F. *Helv. Chem. Acta* 1991, 74, 2054; Seela, F.; Wřner, Rosemeyer, H. *Helv. Chem. Acta* 1994, 77, 883; Seela, F.; Heckel, M.; Rosemeyer, H. *Helv. Chem. Acta* 1996, 79, 1451).

SUMMARY OF THE INVENTION

Based on the above and on the remarkable properties of the 2'-O,4'-C-methylene bridged LNA monomers it was decided to synthesise oligonucleotides comprising one or more 2'-O,4'-C-methylene-β-D-xylofuranosyl nucleotide monomer(s) as the first stereoisomer of LNA modified oligonucleotides. Modelling clearly indicated the xylo-LNA monomers to be locked in an N-type furanose conformation. Whereas the parent 2'-deoxy-β-D-xylofuranosyl nucleosides were shown to adopt mainly an N-type furanose conformation, the furanose ring of the 2'-deoxy-β-D-xylofuranosyl monomers present in xylo-DNA were shown by conformational analysis and computer modelling to prefer an S-type conformation thereby minimising steric repulsion between the nucleobase and the 3'-O-phopshate group (Seela, F.; Wörner, Rosemeyer, H. *Helv. Chem. Acta* 1994, 77, 883). As no report on the hybridisation properties and binding mode of xylo-configurated oligonucleotides in an RNA context was believed to exist, it was the aim to synthesise 2'-O,4'-C-methylene-β-D-xylofuranosyl nucleotide monomer and to study the thermal stability of oligonucleotides comprising this monomer. The results showed that fully modified or almost fully modified Xylo-LNA is useful for high-affinity targeting of complementary nucleic acids. When taking into consideration the inverted stereochemistry at C-3' this is a surprising fact. It is likely that Xylo-LNA monomers, in a sequence context of Xylo-DNA monomers, should have an affinity-increasing effect.

Thus, the present inventors have now provided novel LNA nucleoside analogues (Xylo-LNAs) and oligonucleotides having Xylo-LNA nucleoside analogues included therein. The novel Xylo-LNA nucleoside analogues have been synthesised with thymine as the nucleobase but can easily be synthesised with the other four nucleobases thereby providing a full set of nucleoside analogues for incorporation in oligonucleotides.

The present invention relates to oligomers comprising at least one nucleoside analogue (hereinafter termed "Xylo-LNA") of the general formula I

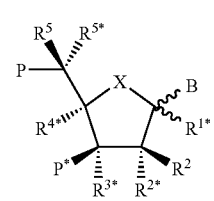

I wherein X is selected from —O—, —S—, —N($R^{N*}$)—, —C($R^6R^{6*}$)—;

B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{2*}$ and $R^{4*}$ designate biradicals consisting of 1–4 groups/atoms selected from —C($R^aR^b$)—, C($R^a$)=C($R^a$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene olefin (=$CH_2$);

each of the substituents $R^{1*}$, $R^2$, $R^{3*}$, $R^5$, $R^{5*}$, $R^6$, and $R^{6*}$ which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(N$R^N$) where $R^N$ is selected from hydrogen and $C_{1-4}$-alkyl, and where two adjacent (non-geminal) substituents may designate an additional bond resulting in a double bond; and $R^{N*}$, when present, is selected from hydrogen and $C_{1-4}$-alkyl;

and basic salts and acid addition salts thereof.

The present invention furthermore relates to nucleoside analogues (Xylo-LNAs) of the general formula II

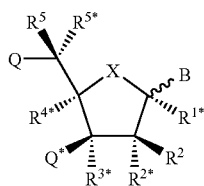

II wherein the substituent B is selected from nucleobases, DNA intercalators, photochemically active groups, thermochemically active groups, chelating groups, reporter groups, and ligands;

X is selected from —O—, —S—, —N($R^{N*}$)—, and —C($R^6R^{6*}$)—;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl; and $R^{2*}$ and $R^{4*}$ together designate a biradical selected from —O—, —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—N(R*)—(CR*R*)$_{r+s}$—N(R*)—, —N(R*)—(CR*R*)$_{r+s}$—S— and —S—(CR*R*)$_{r+s}$—N(R*)—;

wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0–3 with the proviso that the sum r+s is 1–4;

each of the present substituents $R^{1*}$, $R^2$, $R^{3*}$, $R^5$, $R^{5*}$, $R^6$, and $R^{6*}$ is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12*}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(N$R^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof;

with the proviso that any chemical group (including any nucleobase), which is reactive under the conditions prevailing in oligonucleotide synthesis, is optionally functional group protected.

The present invention also relates to the use of the nucleoside analogues (Xylo-LNAs) for the preparation of oligomers, and the use of the oligomers as well as the nucleoside analogues (Xylo-LNAs) in diagnostics, molecular biology research, and in therapy.

DETAILED DESCRIPTION OF THE INVENTION

When used herein, the term "Xylo-LNA" (Xylo-configurated Locked Nucleoside Analogues) refers to xylo-configurated bicyclic nucleoside analogues, either incorporated in the oligomer of the invention (general formula 1) or as discrete chemical species (general formula II). The term "monomeric Xylo-LNA" specifically refers to the latter case.

Oligomers and Nucleoside Analogues

As mentioned above, the present invention i.a. relates to novel oligomers (oligonucleotides) comprising one or more xylo-configurated bicyclic nucleoside analogues. The xylo-configurated bicyclic nucleoside analogues are hereinafter referred to as "Xylo-LNA".

Each of the possible Xylo-LNAs incorporated in an oligomer (oligonucleotide) has the general formula I

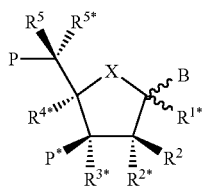

wherein X is selected from —O— (the xylofuranose motif), —S—, —N($R^{N*}$)—, —C($R^6R^{6*}$)—, where $R^6$, $R^{6*}$, and $R^{N*}$ are as defined further below. Thus, the Xylo-LNAs incorporated in the oligomer comprise a 5-membered ring as an essential part of the bicyclic structure.

Among the possible 5-membered rings, the situations where X designates —O—, —S—, and —N($R^{N*}$)— seem especially interesting, and the situation where X is —O— appears to be particularly interesting.

The substituent B may designate a group which, when the oligomer is complexing with DNA or RNA, is able to interact (e.g. by hydrogen bonding or covalent bonding or electronic interaction) with DNA or RNA, especially nucleobases of DNA or RNA. Alternatively, the substituent B may designate a group which acts as a label or a reporter, or the substituent B may designate a group (e.g. hydrogen) which is expected to have little or no interactions with DNA or RNA. Thus, the substituent B is preferably selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosine, $N^6$,$N^6$-ethano-2,6-diaminopurine, 5-methylcytosine, 5-($C^3$–$C^6$)-alkynylcytosine, 5-fluorouracil, 5-bromouracil, pseudoiso-cytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

When used herein, the term "DNA intercalator" means a group that can intercalate into a DNA or RNA helix, duplex or triplex. Examples of functional parts of DNA intercalators are acridines, anthracenes, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline), ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphthoquinone, anthraquinone, naphthoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that comprises more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group that is detectable either by itself or as a part of a detection series. Examples of functional parts of reporter groups are biotin, digoxigenin, fluorescent groups (groups which are able to absorb electromagnetic radiation, e.g. light or X-rays, of a certain wavelength, and which subsequently re-emits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, europium, ruthenium, samarium, and other rare earth metals, radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glucose oxidases), antigens, antibodies, haptens (groups which are able to combine with an antibody, but which cannot initiate an immune response by themselves, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, ruthenium, europium, Cy5 and Cy3.

In the present context, the term "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_{1-20}$ alkyl groups optionally interrupted or terminated with one or more heteroatoms such as oxygen atoms, nitrogen atoms, and/or sulphur atoms, optionally comprising aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It will be clear for the person skilled in the art that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K-where M is the "active/functional" part of the group in question and where K is a spacer through which the "active/functional" part is attached to the 5-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1–50 atoms, preferably 1–30 atoms, in particular 1–15 atoms, between the 5-membered ring and the "active/functional" part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers is less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5-membered ring. In particularly interesting embodiments, the spacer includes a chemically cleavable group. Examples of such chemically cleavable groups include disulphide groups cleavable under reductive conditions, peptide fragments cleavable by peptidases, etc.

In one embodiment of the present invention, K designates a single bond so that the "active/functional" part of the group in question is attached directly to the 5-membered ring.

In a preferred embodiment, the substituent B in the general formulae I and II is preferably selected from nucleobases, in particular from adenine, guanine, thymine, cytosine and uracil.

In the oligomers of the present invention (formula I), P designates the radical position for an internucleoside linkage to a succeeding monomer, or to a 5'-terminal group. The former possibility applies when the Xylo-LNA in question is not the 5'-terminal "monomer", whereas the latter possibility applies when the Xylo-LNA in question is the 5'-terminal "monomer". It should be understood (which also will be clear from the definition of internucleoside linkage and 5'-terminal group further below) that such an internucleoside linkage or 5'-terminal group may include the substituent $R^5$ (or equally applicable: the substituent $R^{5*}$) thereby forming a double bond to the group P. (5'-Terminal refers to the position corresponding to the 5' carbon atom of a ribose moiety in a nucleoside)

On the other hand, P* designates the radical position for an internucleoside linkage to a preceding monomer or a 3'-terminal group. Analogously, the former possibility applies when the Xylo-LNA in question is not the 3'-terminal "monomer", whereas the latter possibility applies when the Xylo-LNA in question is the 3'-terminal "monomer" (3'-terminal refers to the position corresponding to the 3'-carbon atom of a ribose moiety in a nucleoside.)

In the present context, the term "monomer" relates to naturally occurring nucleosides, non-naturally occurring nucleosides, PNAs, LNAs etc. as well as Xylo-LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an Xylo-LNA monomer, may be naturally occurring nucleosides or non-naturally occurring nucleosides, or even further Xylo-LNA monomers.

Consequently, in the present context (as can be derived from the definitions above), the term "oligomer" means an oligonucleotide modified by the incorporation of one or more Xylo-LNA(s). Furthermore, the term "oligomer" means an oligonucleotide modified by the incorporation of one or more Xylo-LNA(s) and one or more "monomers" as defined supra.

The crucial part of the present invention is the xylo-configuration of the 5-membered ring combined with the provision that $R^{2*}$ and $R^{4*}$ together designate a biradical forming a fused ring onto the 5-membered ring.

In the groups constituting the biradical(s), Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted. Moreover, two geminal substituents $R^a$ and $R^b$ together may designate optionally substituted methylene (=$CH_2$ optionally substituted one or two times with substituents as defined as optional substituents for aryl).

It is believed that biradicals which are bound to the ring atoms of the 5-membered rings are preferred in that inclusion of the substituents $R^5$ and $R^{5*}$ may cause an undesired sterical interaction with internucleoside linkage. Thus, it is preferred that the one or two pairs of non-geminal substituents, which are constituting one or two biradical(s), respectively, are selected from the present substituents of $R^{1*}$, $R^6$, $R^6$, $R^{N*}$, $R^2$, and $R^{3*}$.

In the present context, i.e. in the present description and claims, the orientation of the biradicals are so that the left-hand side represents the substituent with the lowest number and the right-hand side represents the substituent with the highest number. Thus, when $R^{2*}$ and $R^4$ together designate a biradical "—O—$CH_2$—", it is understood that the oxygen atom represents $R^{2*}$ and the methylene group represents $R^{4*}$.

Considering the interesting possibilities for the structure of the biradical(s) in Xylo-LNA(s) incorporated in oligomers according to the invention, it is believed that the biradical(s) constituted by pair(s) of non-geminal substituents preferably is/are selected from —(CR*R*)$_r$—Y—(CR*R*)$_s$—, —(CR*R*)$_r$—Y—(CR*R*)$_s$—Y—, —Y—(CR*R*)$_{r+s}$—Y—, —Y—(CR*R*)$_r$—Y—(CR*R*)$_s$—, —(CR*R*)$_{r+s}$—, —Y—, —Y—Y—, wherein each Y is independently selected from —O—, —S—, —Si(R*)$_2$—, —N(R*)—, >C=O, —C(=O)—N(R*)—, and —N(R*)—C(=O)—, each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0–4 with the proviso that the sum r+s is 1–4. Particularly interesting situations are those wherein each biradical is independently selected from —Y—, —(CR*R*)$_{r+s}$—, —(CR*R*)$_r$—Y—(CR*R*)$_s$—, and —Y—(CR*R*)$_{r+s}$—Y—, wherein and each of r and s is 0–3 with the proviso that the sum r+s is 1–4.

Particularly interesting oligomers are those wherein the following criteria applies for the Xylo-LNA(s) in the oligomers: $R^{2*}$ and $R^{4*}$ together designate a biradical selected from —O—, —S—, —N(R*)—, —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—, —S—(CR*R*)$_{r+s}$—O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—; wherein each of r and s is 0–3 with the proviso that the sum r+s is 1–4, and where R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

In one preferred embodiment, one group R* in the biradical of at least one LNA is selected from DNA intercalators, photochemically active groups, thermochemically active groups, chelating groups, reporter groups, and ligands (where the latter groups may include a spacer as defined for the substituent B).

In another preferred embodiment, one group R* in the biradical of at least one LNA is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

With respect to the substituents $R^{1*}$, $R^2$, $R^3$, $R^5$, $R^{5*}$, $R^6$, and $R^{6*}$ which are present, are independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present, is selected from hydrogen and C$_{1-4}$-alkyl.

Preferably, each of the substituents R$^{1*}$, R$^2$, R$^{3*}$, R$^5$, R$^{5*}$, R$^6$, and R$^{6*}$ of the Xylo-LNA(s), which are present, is independently selected from hydrogen, optionally substituted C$_{1-6}$-alkyl, optionally substituted C$_{2-6}$-alkenyl, hydroxy, C$_{1-6}$-alkoxy, C$_{2-6}$-alkenyloxy, carboxy, C$_{1-6}$-alkoxycarbonyl, C$_{1-6}$-alkylcarbonyl, formyl, amino, mono- and di(C$_{1-6}$-alkyl)amino, carbamoyl, mono- and di(C$_{1-6}$-alkyl)-amino-carbonyl, C$_{1-6}$-alkyl-carbonylamino, carbamido, azido, C$_{1-6}$-alkanoyloxy, sulphono, sulphanyl, C$_{1-6}$-alkylthio, DNA intercalators, photochemically active groups, thermochemically active groups, chelating groups, reporter groups, and ligands, and halogen, where two geminal substituents together may designate oxo, and where R$^{N*}$, when present, is selected from hydrogen and C$_{1-4}$-alkyl.

In a preferred embodiment of the present invention, X is selected from —O—, —S—, and —NR$^{N*}$, in particular —O—, and each of the substituents R$_{1*}$, R$^2$, R$^{3*}$, R$^5$, R$^{5*}$, R$^6$, and R$^{6*}$ of the Xylo-LNA(s), which are present, designate hydrogen.

In an even more preferred embodiment of the present invention, X is —O—, the substituents R$^{1*}$, R$^2$, R$^3$, R$^5$, and R$^{5*}$ designate hydrogen, and R$^{2*}$ and R$^{4*}$ of an Xylo-LNA incorporated into an oligomer together designate a biradical, selected from —O—, —(CH$_2$)$_{0-1}$—O—(CH$_2$)$_{1-3}$—, —(CH$_2$)$_{0-1}$—S—(CH$_2$)$_{1-3}$—, —(CH$_2$)$_{0-1}$—N(R$^N$)—(CH$_2$)$_{1-3}$—, and —(CH$_2$)$_{2-4}$—, in particular from —O—CH$_2$—, —S—CH$_2$—, and —NR$^H$—CH$_2$—. Generally, with due regard to the results obtained so far, it is preferred that the biradical constituting R$^{2*}$ and R$^{4*}$ forms a two atom bridge, i.e. the biradical forms a five membered ring with the furanose ring (X=O).

In one embodiment of the present invention the biradical is —(CH$_2$)$_{2-4}$—.

For these interesting embodiments, it is preferred that the Xylo-LNA(s) has/have the following general formula Ia.

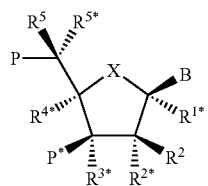

Ia

Also interesting as a separate aspect of the present invention is the variant of formula Ia where B is in the "α-configuration".

The oligomers according to the invention typically comprise 1–10000 Xylo-LNA(s) of the general formula I (or of the more detailed general formula Ia) and 0–10000 nucleosides selected from naturally occurring nucleosides and nucleoside analogues. The sum of the number of nucleosides and the number of Xylo-LNA(s) (n) is at least 2, preferably at least 3, in particular at least 5, especially at least 7, such as in the range of 2–15000, preferably in the range of 2–100, such as 3–100, in particular in the range of 2–50, such as 3–50 or 5–50 or 7–50.

It has been found that partly- and fully LNA modified oligomers with all ribo-configuration hybridise strongly (with increasing affinity) to DNA, RNA and other ribo-configurated LNA oligomers. It is presently believed that fully Xylo-LNA modified oligomers and oligomers consisting of Xylo-LNA monomers and other xylo-configurated nucleoside analogues, e.g., 2'-deoxyonucleosides, will give rise to comparable hybridisation properties. It has been shown that hybridisation of an LNA modified oligomer with another all ribo-configurated oligomer, e.g., DNA, RNA or another all ribo-configurated LNA modified oligomer, will give rise to an anti-parallel orientation of the two oligomers and increased affinity. It is thus contemplated that hybridisation of an all xylo-configurated Xylo-LNA modified oligomer with DNA, RNA or ribo-configurated LNA oligomer will give rise to parallel orientation of the oligomers.

In view of the above, it is contemplated that the combination of ribo-configurated LNAs and xylo-LNAs in one oligomer can give rise to interesting properties as long as these monomers of different configurations are located in domains, i.e. so that an uninterrupted domain of at least 5, such as at least 10, preferably at least 13 monomers of, e.g., Xylo-LNAs, other xylo-configurated nucleotide monomers, or Xylo-LNA together with other xylo-configurated nucleotide monomers, is followed by an uninterrupted domain of at least 5, such as at least 10, monomers of the other type (e.g. ribo-configurated LNA, ribonucleotides, 2'-deoxyribonucleotides, etc.). Such chimeric type oligomers may, e.g., be used to capture nucleic acids.

In a preferred embodiment of the present invention, the modified oligonucleotides comprises at least 7, preferably at least 9, in particular at least 11, especially at least 13 successive Xylo-LNA monomers. In one embodiment of the invention, the continuous stretch of Xylo-LNAs is arranged in one or more domain(s) in a modified oligonucleotide.

In a preferred embodiment of the invention, the continuous stretch of Xylo-LNAs is arranged in one or more domain(s) together within adjacent stretches of Xylo-DNA or Xylo-RNA.

In a more preferred embodiment of the present invention, the ratio between the number of nucleotides and the number of Xylo-LNA monomers in a modified oligonucleotide is 1:n−1 wherein n is the total sum of nucleotides and Xylo-LNA monomers in the oligonucleotide.

In an even more preferred embodiment of the invention, all nucleoside monomers in an oligomer are Xylo-LNA.

Preferably at least one Xylo-LNA comprises a nucleobase as the substituent B.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and non-naturally occurring) and nucleoside analogues (including known bi- and tricyclic analogues), it is clear that an oligomer may comprise one or more Xylo-LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above.

The oligomers may be linear, branched or cyclic. In the case of a branched oligomer, the branching points may be located in a nucleoside, in an internucleoside linkage or, in an intriguing embodiment, in an Xylo-LNA. It is believed that in the latter case, the substituents $R^2$, and $R^{3*}$ may designate a group P* designating an internucleoside linkage to a preceding monomer, in particular, $R^2$ designate a further P*.

As mentioned above, the Xylo-LNA(s) of an oligomer are connected with other monomers via an internucleoside linkage. In the present context, the term "internucleoside linkage" means a linkage consisting of 2 to 4, preferably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected form hydrogen and $C_{1-4}$-alkyl, and R" is selected from $C_{1-6}$-alkyl and phenyl. Illustrative examples of such internucleoside linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2CH_2$—, —$CH_2CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,NR$^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,NR$^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl, are especially preferred. Further illustrative examples are given in Mesmaeker et. al., *Current Opinion in Structural Biology* 1995, 5, 343–355. The left-hand side of the internucleoside linkage is bound to the 5-membered ring as substituent P*, whereas the right-hand side is bound to the 5'-position of a preceding monomer.

It is also clear from the above that the group P may also designate a 5'-terminal group in the case where the Xylo-LNA in question is the 5'-terminal monomer. Examples of such 5'-terminal groups are hydrogen, hydroxy, optionally substituted $C_{1-6}$-alkyl, optionally substituted $C_{1-6}$-alkoxy, optionally substituted $C_{1-6}$-alkylcarbonyloxy, optionally substituted aryloxy, monophosphate, diphosphate, triphosphate, and —W—A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—P(O)$_2$—O$^-$, —O—P(O)$_2$—O—P(O)$_2$—O$^-$, and —O—P(O)$_2$—O—P(O)$_2$—O—P(O)$_2$—O$^-$, respectively.

In a particularly interesting embodiment, the group P designates a 5'-terminal groups selected from monophosphate, diphosphate and triphosphate. Especially the triphosphate variant is interesting as a substrate.

Analogously, the group P* may designate a 3'-terminal group in the case where the Xylo-LNA in question is the 3'-terminal monomer. Examples of such 3'-terminal groups are hydrogen, hydroxy, optionally substituted $C_{1-6}$-alkoxy, optionally substituted $C_{1-6}$-alkylcarbonyloxy, optionally substituted aryloxy, and —W—A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In a preferred embodiment of the present invention, the oligomer has the following formula V:

$$G\text{-}[Nu\text{—}L]_{n(0)}\text{-}\{[Xylo\text{-}LNA\text{-}L]_{m(q)}\text{-}[Nu\text{-}L]_{n(q)}\}_q\text{-}G^* \qquad V$$

wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each Xylo-LNA independently designates a nucleoside analogue;

each L independently designates an internucleoside linkage between two groups selected from Nu and Xylo-LNA, or L together with G* designates a 3'-terminal group; and each Xylo-LNA-L independently designates a nucleoside analogue of the general formula I as defined above, or preferably of the general formula Ia as defined above.

Within this embodiment, as well as generally, the present invention provides the intriguing possibility of including Xylo-LNAs with different nucleobases, in particular both nucleobases selected from thymine, cytosine and uracil and nucleobases selected from adenine and guanine.

Apart from the oligomers defined above, the present invention also provides monomeric Xylo-LNAs useful in, for example, the preparation of oligomers, as substrates for, e.g., nucleic acid polymerases, polynucleotide kinases, terminal transferases, and as therapeutic agents (see further below). The monomeric Xylo-LNAs correspond in overall structure (especially with respect to the possible biradicals) to the Xylo-LNAs defined as constituents in oligomers. However, with respect to the groups P and P*, the monomeric Xylo-LNAs differ slightly to those consituent in oligomers, as will be explained below. Furthermore, the monomeric Xylo-LNAs may comprise functional group protecting groups, especially in the cases where the monomeric Xylo-LNAs are to be incorporated into oligomers by chemical synthesis.

The invention furthermore relates to monomeric Xylo-LNA nucleosides (Xylo-LNAs) of the general formula II

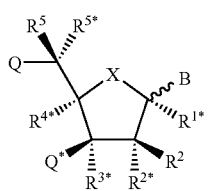

wherein the substituent B is selected from nucleobases, DNA intercalators, photochemically active groups, thermochemically active groups, chelating groups, reporter groups, and ligands; X is selected from —O—, —S—, —N($R^{N*}$)—, and —C($R^6R^{6*}$)—, preferably from —O—, —S—, and —N($R^{N*}$)—;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $_{1-6}$-alkyl;

$R^{2*}$ and $R^{4*}$ together designate a biradical selected from —O—, —S—, —N(R*)—, —(CR*R*)$_{r+s+1}$—; —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—; wherein R* is as defined above for the oligomers; and each of the substituents $R^{1*}$, $R^2$, $R^{3*}$, $R^5$, and $R^{5*}$, which are not involved in Q, or Q*, are as defined above for the oligomers.

The monomeric Xylo-LNAs also comprise basic salts and acid addition salts thereof.

Furthermore, it should be understood that any chemical group (including any nucleobase), which is reactive under the conditions prevailing in chemical oligonucleotide synthesis, is optionally functional group protected as known in the art. This means that groups such as hydroxy, amino, carboxy, sulphono, and mercapto groups, as well as nucleobases, of a monomeric Xylo-LNA are optionally functional group protected. Protection (and deprotection) is performed by methods known to the person skilled in the art (see, e.g., Greene, T. W. and Wuts, P. G. M., "Protective Groups in Organic Synthesis", $2^{nd}$ ed., John Wiley, N.Y. (1991), and M. J. Gait, Oligonucleotide Synthesis, IRL Press, 1984).

Illustrative examples of hydroxy protection groups are optionally substituted trityl, such as 4,4'-dimethoxytrityl (DMT), 4-monomethoxytrityl (MMT), and trityl (Tr), optionally substituted 9-(9-phenyl)xanthenyl (pixyl), optionally substituted ethoxycarbonyloxy, p-phenylazophenyloxycarbonyloxy, tetraahydropyranyl (thp), 9-fluorenylmethoxycarbonyl (Fmoc), methoxytetrahydropyranyl (mthp), silyloxy such as trimethylsilyl (TMS), triisopropylsilyl (TIPS), tert-butyldimethylsilyl (TBDMS), triethylsilyl, and phenyldimethyl-silyl, benzyloxycarbonyl or substituted benzyloxycarbonyl ethers such as 2-bromo benzyloxycarbonyl, tert-butylethers, alkyl ethers such as methyl ether, acetals (including two hydroxy groups), acyloxy such as acetyl or halogen substituted acetyls, e.g. chloroacetyl orfluoroacetyl, isobutyryl, pivaloyl, benzoyl and substituted benzoyl, methoxymethyl (MOM), benzyl ethers or substituted benzyl ethers such as 2,6-dichlorobenzyl (2,6-$Cl_2$Bzl). Alternatively, the hydroxy group may be protected by attachment to a solid support optionally through a linker.

Illustrative examples of amino protection groups are Fmoc (fluorenylmethoxycarbonyl), BOC (tert-butyloxycarbonyl), trifluoroacetyl, allyloxycarbonyl (alloc, AOC), benzyl-oxycarbonyl (Z, Cbz), substituted benzyloxycarbonyls such as 2-chloro benzyloxycarbonyl ((2-ClZ), monomethoxytrityl (MMT), dimethoxytrityl (DMT), phthaloyl, and 9-(9-phenyl) xanthenyl (pixyl).

Illustrative examples of carboxy protection groups are allyl esters, methyl esters, ethyl esters, 2-cyanoethylesters, trimethylsilylethylesters, benzyl esters (Obzl), 2-adamantyl esters (O-2-Ada), cyclohexyl esters (OcHex), 1,3-oxazolines, oxazoler, 1,3-oxazolidines, amides or hydrazides.

Illustrative examples of mercapto protecting groups are trityl (Tr), acetamidomethyl (acm), trimethylacetamidomethyl (Tacm), 2,4,6-trimethoxybenzyl (Tmob), tert-butylsulfenyl (StBu), 9-fluorenylmethyl (Fm), 3-nitro-2-pyridinesulfenyl (Npys), and 4-methylbenzyl (Meb).

Furthermore, it may be necessary or desirable to protect any nucleobase included in a monomeric Xylo-LNA, especially when the monomeric Xylo-LNA is to be incorporated in an oligomer according to the invention. In the present context, the term "protected nucleobases" means that the nucleobase in question is carrying a protection group selected among the groups which are well-known for a man skilled in the art (see e.g. Protocols for Oligonucleotides and Analogs, vol 20, (Sudhir Agrawal, ed.), Humana Press, 1993, Totowa, N.J.; S. L. Beaucage and R. P. Iyer, Tetrahedron, 1993, 49, 6123; S. L. Beaucage and R. P. Iyer, Tetrahedron, 1992, 48, 2223; and E. Uhlmann and A. Peyman, Chem. Rev., 90, 543.). Illustrative examples are benzoyl, isobutyryl, tert-butyl, tert-butyloxycarbonyl, 4-chloro-benzyloxycarbonyl, 9-fluorenylmethyl, 9-fluorenylmethyloxycarbonyl, 4-methoxybenzoyl, 4-methoxytriphenylmethyl, optionally substituted triazolo, p-toluenesulphonyl, optionally substituted sulphonyl, isopropyl, optionally substituted amidines, optionally substituted trityl, phenoxyacetyl, optionally substituted acyl, pixyl, tetrahydropyranyl, optionally substituted silyl ethers, and 4-methoxybenzyloxycarbonyl. Chapter 1 in "Protocols for oligonucleotide conjugates", Methods in Molecular Biology, vol 26, (Sudhir Agrawal, ed.), Humana Press, 1993, Totowa, N.J. and S. L. Beaucage and R. P. Iyer, *Tetrahedron,* 1992, 48, 2223 disclose further suitable examples.

In a preferred embodiment, the group B in a monomeric Xylo-LNA is preferably selected from nucleobases and protected nucleobases.

In an embodiment of the monomeric Xylo-LNAs according to the present invention, one of Q and Q*, preferably Q*, designates a group selected from Act-O—, Act-S—, Act-N($R^H$)—, Act-O—$CH_2$—, Act-S—$CH_2$—, Act-N($R^H$)—$CH_2$—, and the other of Q and Q*, preferably Q, designates a group selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, aminomethyl, Prot-N($R^H$)—$CH_2$—, carboxymethyl, sulphonomethyl, and $R^H$ is selected from hydrogen and $C_{1-6}$-alkyl.

In the case described above, the group Prot designates a protecting group for —OH, —SH, and —NH($R^H$), respectively. Such protection groups are selected from the same as defined above for hydroxy protection groups, mercapto protection group, and amino protection groups, respectively, however taking into consideration the need for a stable and reversible protection group. However, it is preferred that any protection group for —OH is selected from optionally substituted trityl, such as dimethoxytrityl (DMT), monomethoxytrityl (MMT), and trityl, and 9-(9-phenyl)xanthenyl (pixyl), optionally substituted, tetrahydropyranyl (thp) (further suitable hydroxy protection groups for phosphoramidite oligonucleotide synthesis are described in Agrawal, ed. "Protocols for Oligonucleotide Conjugates"; Methods in Molecular Biology, vol. 26, Humana Press, Totowa, N.J. (1994) and Protocols for Oligonucleotides and Analogs, vol 20, (Sudhir Agrawal, ed.), Humana Press, 1993, Totowa, N.J.), or protected as acetal; that any protection group for —SH is selected from trityl, such as dimethoxytrityl (DMT), monomethoxytrityl (MMT), and trityl (Tr), and 9-(9-phenyl)xanthenyl (pixyl), optionally substituted, tetrahydropyranyl (thp) (further suitable mercapto protection groups for phosphoramidite oligonucleotide synthesis are also described in Agrawal (see above); and that any protecting group for —NH($R^H$) is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable amino protection groups for phosphoramidite oligonucleotide synthesis are also described by Agrawal (see above).

In the embodiment above, as well as for any monomeric Xylo-LNAs defined herein, Act designates an activation group for —OH, —SH, and —NH($R^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, or benzyl, and each of $R^y$ designate optionally substituted alkyl groups, e.g. ethyl or isopropyl, or the group —N($R^y$)$_2$ forms a morpholino group (—N($CH_2CH_2$)$_2$O). $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

It should be understood that the protecting groups used herein for a single monomeric Xylo-LNA or several monomeric Xylo-LNAs may be selected so that when this/these Xylo-LNA(s) are incorporated in an oligomer according to the invention, it will be possible to perform either a simultaneous deprotection or a sequential deprotection of the functional groups. The latter situation opens for the possibility of regioselectively introducing one or several "active/functional" groups such as DNA intercalators, photochemically active groups, thermochemically active groups, chelating groups, reporter groups, and ligands, where such groups may be attached via a spacer as described above.

In a preferred embodiment, Q is selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, aminomethyl, Prot-N($R^H$)—$CH_2$—, carboxymethyl, sulphonomethyl, where Prot is a protection group for —OH, —SH, and —NH($R^H$), respectively, and $R^H$ is selected from hydrogen and $C_{1-6}$-alkyl; and Q* is selected from hydrogen, azido, halogen, cyano, nitro, hydroxy, Act-O—, mercapto, Act-S—, $C_{1-6}$-alkylthio, amino, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, DNA intercalators, photochemically active groups, thermochemically active groups, chelating groups, reporter groups, ligands, carboxy, sulphono, where Act is an activation group for —OH, —SH, and —NH($R^H$), respectively, and $R^H$ is selected from hydrogen and $C_{1-6}$-alkyl.

The monomeric Xylo-LNAs of the general formula II may, as the Xylo-LNAs incorporated into oligomers, represent various stereoisomers. Thus, the stereochemical variants described above for the Xylo-LNAs incorporated into oligomers are believed to be equally applicable in the case of monomeric Xylo-LNAs (however, it should be noted that P should then be replaced with Q).

In a preferred embodiment of the present invention, the monomeric LNA has the general formula IIa

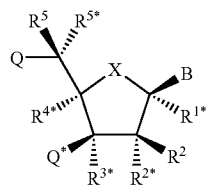

IIa wherein the substituents are defined as above.

Furthermore, with respect to the definitions of substituents, biradicals, R*, etc. the same preferred embodiments as defined above for the oligomer according to the invention also apply in the case of monomeric Xylo-LNAs.

In a particularly interesting embodiment of the monomeric Xylo-LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —$(CH_2)_{0-1}$—O—$(CH_2)_{1-3}$—, —$(CH_2)_{0-1}$—S—$(CH_2)_{1-3}$—, and —$(CH_2)_{0-1}$—N($R^N$)—$(CH_2)_{1-3}$—, in particular —O—$CH_2$—, —S—$CH_2$— and —$R^N$—$CH_2$—, where $R^N$ is selected from hydrogen and $C_{1-4}$-alkyl, Q designates Prot-O—, Q* designates Act-OH, and $R^{1*}$, $R^2$, $R^3$, $R^5$, and $R^{5*}$ each designate hydrogen. In this embodiment, $R^N$ may also be selected from DNA intercalators, photochemically active groups, thermochemically active groups, chelating groups, reporter groups and ligands.

In a further particularly interesting embodiment of the monomeric Xylo-LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —$(CH_2)_{0-1}$—O—$(CH_2)_{1-3}$—, —$(CH_2)_{0-1}$—S—$(CH_2)_{1-3}$—, and —$(CH_2)_{0-1}$—N($R^N$)—$(CH_2)_{1-3}$—, in particular —O—$CH_2$—, —S—$CH_2$— and —$R^N$—$CH_2$—, where $R^N$ is selected from hydrogen and $C_{1-4}$-alkyl, Q is selected from hydroxy, mercapto, $C_{1-6}$-alkylthio, amino, mono- or di($C_{1-6}$-alkyl)amino, optionally substituted $C_1$-alkoxy, optionally substituted $C_{2-6}$-alkenyloxy, optionally substituted $C_{2-6}$-alkynyloxy, monophosphate, diphosphate, and triphosphate, Q* is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, $R^{3*}$ is selected from hydrogen, optionally substituted $C_{1-6}$-alkyl, optionally substituted $C_{2-6}$-alkenyl, and optionally substituted $C_{2-6}$-alkynyl, and $R^{1*}$, $R^2$, $R^5$, and $R^{5*}$ each designate hydrogen. Also here, $R^N$ may also be selected from DNA intercalators, photochemically active groups, thermochemically active groups, chelating groups, reporter groups and ligands.

One aspect of the invention is to provide various derivatives of Xylo-LNAs for solid-phase and/or solution phase incorporation into an oligomer. As an illustrative example, monomers suitable for incorporation of (1S,3R,4R,7R)-7-hydroxy-1-hydroxymethyl-3-(thymin-1-yl)-2,5-dioxabicyclo[2.2.1]heptane, (IS, 3R, 4R, 7R)-7-hydroxy-1-hydroxymethyl-3-(cytosin-1-yl)-2,5-dioxabicyclo[2.2.1]heptane, (1S,3R,4R,7R)-7-hydroxy-1-hydroxymethyl-3-(uracil-1-yl)-2,5-dioxabicyclo[2.2.1]heptane, (IS,3R,4R,7R)-7-hydroxy-1-hydroxymethyl-3-(guanin-1-yl)-2,5-dioxabicyclo[2.2.1] heptane, and (1S,3R,4R,7R)-7-hydroxy-1-hydroxymethyl-3-(adenin-1-yl)-2,5-dioxabicyclo[2.2.1]heptane using the phosphoramidite approach, the phosphortriester approach, and the H-phosphonate approach, respectively, are (1R,3R,4R,7R)-7-(2-Cyanoethoxy(diisopropylamino) phosphinoxy)-1-(4,4'-dimethoxytrityloxymethyl)-3-(thymin-1-yl)-2,5-dioxabi-cyclo[2.2.1]heptane, (1R,3R,4R,7R)-7-hydroxy-1-(4,4'-dimethoxytrityloxymethyl)-3-(thymin-1-yl)-2,5-dioxabicyclo[2.2.1]heptane-7—O—(2-chlorophenylphosphate), and (1R,3R,4R,7R)-7-hydroxy-1-(4,4'-dimethoxytrityloxymethyl)-3-(thymin-1-yl)-2,5-dioxabicyclo[2.2.1]heptane-7—O—(H-phosphonate) and the 3-(cytosin-1-yl), 3-(uracil-1-yl), 3-(adenin-1-yl) and 3-(guanin-1-yl) analogues thereof, respectively. Furthermore, the analogues where the methyleneoxy biradical of the monomers is substituted with a methylenethio, a methyleneamino, or a 1,2-ethylene biradical are also expected to constitute particularly interesting variants within the present invention. The methylenethio and methyleneamino analogues are believed to be equally applicable as the methyleneoxy analogue and therefore the specific reagents corresponding to those mentioned for incorporation of (1S,3R,4R,7R)-7-hydroxy-1-hydroxymethyl-3-(thymin-1-yl)-2,5-dioxabicyclo[2.2.1]heptane, (1S,3R,4R,7R)-7-hydroxy-1-hydroxymethyl-3-(cytosin-1-yl)-2,5-dioxabicyclo[2.2.1] heptane, (1S,3R,4R,7R)-7-hydroxy-1-hydroxymethyl-3-(uracil-1-yl)-2,5-dioxabicyclo[2.2.1]heptane, (1S,3R,4R, 7R)-7-hydroxy-1-hydroxymethyl-3-(guanin-1-yl)-2,5-dioxabicyclo[2.2.1]heptane, and (1S,3R,4R,7R)-7-hydroxy-1-hydroxymethyl-3-(adenin-1-yl)-2,5-dioxabicyclo[2.2.1] heptane should also be considered as particularly interesting reactive monomers within the present invention. For the methyleneamine analogue, it should be noted that the secondary amine may carry a substituent selected from optionally substituted $C_{1-6}$-alkyl such as methyl and benzyl, optionally substituted $C_{1-6}$-alkylcarbonyl such as trifluoroacetyl, optionally substituted arylcarbonyl and optionally substituted heteroarylcarbonyl.

Preparation of Monomers

In a preferred embodiment, Xylo-LNA containing a 2'-O, 4'-C-methylene bridge was synthesised by the following procedure:

Synthesis of xylo-configured nucleosides (Rosemeyer, H.; Seela, F. *Helv. Chem. Acta* 1991, 74, 748; Rosemeyer, H.; Krecmerova, M.; Seela, F. *Helv. Chem. Acta* 1991, 74, 2054; Seela, F.; Wörner, Rosemeyer, H. *Helv. Chem. Acta* 1994, 77, 883; Seela, F.; Heckel, M.; Rosemeyer, H. *Helv. Chem. Acta* 1996, 79, 1451) and a number of 4'-C-hydroxymethyl nucleosides (R. D. Youssefyeh, J. P. H. Verheyden and J. G. Moffatt, *J. Org. Chem.*, 1979, 44, 1301; G. H. Jones, M. Taniguchi, D. Tegg and J. G. Moffatt, *J. Org. Chem.*, 1979, 44, 1309; C. O-Yang, H. Y. Wu, E. B. Fraser-Smith and K. A. M. Walker, *Tetrahedron Lett.*, 1992, 33, 37; H. Thrane, J. Fensholdt, M. Regner and J. Wengel, *Tetrahedron*, 1995, 51, 10389; K. D. Nielsen, F. Kirpekar, P. Roepstorff and J. Wengel, *Bioorg. Med. Chem.*, 1995, 3, 1493) have been reported earlier. However, no examples of 4'-C-hydroxymethyl xylo-nucleosides and the corresponding 2'-O,4'-C-methylene xylo-LNA have been reported. For exemplification of the synthesis of 2'-O,4'-C-methylene xylo-LNA we chose a strategy starting from 4'-C-hydroxymethyl furanose derivative 1 (Tam, T. F., Fraser-Ried, B., *Can. J. Chem.*, 1979, 57, 2818). Benzylation, acetolysis, and acetylation afforded xylo-furanose 3, a key intermediate for nucleoside coupling. Stereoselective reaction with silylated thymine afforded compound 4 which was deacetylated to give nucleoside triol 5. Tosylation followed by 4,4'-dimethoxytrityl protection afforded the 5'-O-4,4'-dimethoxytrityl protected nucleoside derivative 7. Base-induced ring closure afforded the bicyclic nucleoside derivative 8. Concomitant debenzylation and detritylation yielded the unprotected bicyclic nucleoside analogue 9 which was transformed into the 5'-O-4,4'-dimethoxytrityl protected analogue 10 and subsequently into the phosphoramidite derivative 11 for oligonucleotide synthesis. The coupling method used in the example is only one of several possible methods as will be apparent for a person skilled in the art.

A strategy starting from a preformed nucleoside is also possible. As another example of possible strategies, coupling of a pre-cyclised furanose derivatives with different nucleobase derivatives is possible. Such a strategy would in addition allow preparation of the corresponding α-nucleoside analogues. Incorporation of such α-Xylo-LNA nucleosides will be possible using the standard oligomerisation techniques yielding α-Xylo-LNA oligomers. In addition, a synthetic strategy performing nucleoside coupling using a 4'-C-hydroxymethyl furanose already activated for ring closure (e.g. by containing a mesyl or tosyl group at the 4'-C-hydroxymethyl group), is another possible strategy for synthesis of Xylo-LNA oligomers.

Chemical or enzymatic transglycosylation or anomerisation of appropriate nucleosides are yet other possible synthetic strategies. These and other related strategies allow for synthesis of Xylo-LNAs comprising other nucleobases or nucleobase analogues as well as α-Xylo-LNA oligomers.

The described examples are meant to be illustrative for the procedures and examples of this invention. The structures of the synthesised compounds were verified using 1D NMR.

An additional embodiment of the present invention is to provide bicyclic nucleosides containing rings of different sizes and of different chemical structures. From the methods described it is obvious for a person skilled in the art of organic synthesis that cyclisation of other nucleosides is possible using similar procedures, also of nucleosides containing different C-branches. Regarding rings of different chemical compositions it is clear that these can be obtained by using similar procedures and other procedures well-established in the field of organic chemistry, for example synthesis of thio and amino analogues of the exemplified oxo analogue can be accomplished using for example nucleophilic substitution reactions. Alternative, inversion of the stereochemistry around C-2' before cyclisations and activation of the formed 2'-β-OH, e.g. by tosylation, followed by nucleophilic substitution on the C-2' could furnish the desired bicyclic 2'-thio- or 2'-amino-Xylo-LNA nucleosides.

For the amino Xylo-LNA analogue, protection of the 2'-amino functionality will be needed for controlled linear oligomerisation. Such protection can be accomplished using standard amino group protection techniques like, e.g., Fmoc, trifluoroacetyl or BOC. Alternatively, an N-alkyl group (e.g. benzyl, methyl, ethyl, propyl or functionalised alkyl) can be kept on during nucleoside transformations and oligomerisation.

Properly protected cytosine, guanine, and adenine Xylo-LNA analogues can be prepared for oligomerisation using the standard reactions (DMT-protection and phosphitylation) described above.

Preparation of Oligomers

Linear-, branched-(M. Grøtli and B. S. Sproat, *J. Chem. Soc., Chem. Commun.*, 1995, 495; R. H. E. Hudson and M. J. Damha, *J. Am. Chem. Soc.*, 1993, 115, 2119; M. Von Büren, G. V. Petersen, K. Rasmussen, G. Brandenburg, J. Wengel and F. Kirpekar, *Tetrahedron*, 1995, 51, 8491) and circular- (G. Prakash and E. T. Kool, *J. Am. Chem. Soc.*, 1992, 114, 3523) oligo- and polynucleotides of the invention may be produced using the polymerisation techniques of nucleic acid chemistry well known to a person of ordinary skill in the art of organic chemistry. Phosphoramidite chemistry (S. L. Beaucage and R. P. Iyer, *Tetrahedron*, 1993, 49, 6123; S. L. Beaucage and R. P. Iyer, *Tetrahedron*, 1992, 48, 2223) was used, but e.g. H-phosphonate chemistry, phosphortriester chemistry or enzymatic synthesis could also be used. The standard coupling conditions for the phosphoramidite approach was slightly modified using pyridine hydrochloride instead of 1H-tetrazole as a highly efficient reagent for activating nucleoside phosphoramidites during oligonucleotide synthesis, and a prolongation of the coupling time to between 10 to 30 min.

After synthesis of the desired sequence, deprotection and cleavage from the solid support (cleavage from solid support and removal of protection groups using concentrated ammonia in methanol at room temperature for 12 h and subsequent reversed phase purification using commercially available disposable cartridges (which includes detritylation) yield the final oligomeric product. Alternatively, purification of Xylo-LNA oligonucleotides can be done using disposable reversed phase HPLC and/or precipitation from ethanol or butanol. Capillary gel electrophoresis was used to verify the purity and the composition of the synthesised oligonucleotide analogues. However, purity and composition may also be verified using reversed phase HPLC and MALDI-MS.

Generally, the present invention provides the use of Xylo-LNAs as defined herein for the preparation of Xylo-LNA modified oligonucleotides. It should be understood that Xylo-LNA modified oligonucleotides may comprise normal nucleosides (i.e. naturally occurring nucleosides such as ribonucleosides and/or deoxyribonucleosides), as well as modified nucleosides different from those defined with the general formula II.

Furthermore, solid support materials having immobilised thereto an optionally nucleobase protected and optionally 5'-OH protected LNA are especially interesting as material for the synthesis of LNA modified oligonucleotides where an LNA monomer is included in at the 3' end. In this instance, the solid support material is preferably CPG, e.g. a readily (commercially) available CPG material onto which a 3'-functionalised, optionally nucleobase protected and optionally 5'-OH protected LNA is linked using the conditions stated by the supplier for that particular material. BioGenex Universal CPG Support (BioGenex, U.S.A.), for example, can be used. The 5'-OH protecting group may, e.g., be a DMT group. The 3'-functional group should be selected with due regard to the conditions applicable for the CPG material in question.

Applications

The present invention discloses the surprising finding that derivatives of Xylo-LNAs, when incorporated into partly modified oligonucleotides, decrease the affinity of these modified oligonucleotides for both complementary DNA and RNA compared to the unmodified oligonucleotides. However, when incorporated into fully Xylo-LNA modified oligonucleotides, a dramatic increase in hybridisation properties for both complementary ssDNA and ssRNA is observed. Depending on the application, the use of fully modified Xylo-LNA oligonucleotides thus offers the intriguing possibility to either greatly increase the affinity of a standard oligonucleotide without compromising specificity (constant size of oligonucleotide) or significantly increase the specificity without compromising affinity (reduction in the size of the oligonucleotide).

It is also believed that Xylo-LNA modified oligonucleotides, in addition to greatly enhanced hybridisation properties, display many of the useful physicochemical properties of normal DNA and RNA oligonucleotides. The prospect includes excellent solubility, a response of LNA modified oligonucleotides to salts like sodium chloride and tetramethylammonium chloride which mimic that of the unmodified oligonucleotides, the ability of LNA modified oligonucleotides to act as primers for a variety of polymerases, the ability of LNA modified nucleotides to act as primers in a target amplification reaction using a thermostable DNA polymerase, the ability of LNA modified oligonucleotides to act as a substrate for T4 polynucleotide kinase, the ability of biotinylated LNAs to sequence specifically capture PCR amplicons onto a streptavidine coated solid surface, the ability of immobilised LNA modified oligonucleotides to sequence specifically capture amplicons and very importantly the ability of LNA modified oligonucleotides to sequence specifically target double-stranded DNA by strand invasion. Hence, it is apparent to one of ordinary skills in the art that these novel nucleoside analogues are extremely useful tools to improve the performance in general of oligonucleotide based techniques in therapeutics, diagnostics and molecular biology.

An object of the present invention is to provide monomeric Xylo-LNAs according to the invention which can be incorporated into oligonucleotides using procedures and equipment well known to one skilled in the art of oligonucleotide synthesis.

Another object of the present invention is to provide fully or partly Xylo-LNA modified oligonucleotides (oligomers) that are able to hybridise in a sequence specific manner to complementary oligonucleotides forming either duplexes or triplexes of substantially higher affinity than the corresponding complexes formed by unmodified oligonucleotides.

Another object of the present invention is to use fully Xylo-LNA modified oligonucleotides to obtain enhance specificity of the oligonucleotides without compromising on the affinity.

Another object of the present invention is to provide fully or partly modified oligonucleotides comprising Xylo-LNAs, normal nucleosides and other nucleoside analogues.

A further object of the present invention is to exploit the high affinity of Xylo-LNAs to create fully modified oligonucleotides of extreme affinity that are capable of binding to their target sequences in a dsDNA molecule by way of "strand displacement".

A further object of the invention is to provide different classes of Xylo-LNAs which, when incorporated into oligonucleotides, differ in their affinity towards their complementary nucleosides. This can be achieved for example by substituting the normal nucleobases G, A, T, C and U with derivatives having, for example, altered hydrogen bonding possibilities.

Another object of the present invention is to provide Xylo-LNA modified oligonucleotides which are more resistant to nucleases than their unmodified counterparts.

Another object of the present invention is to provide Xylo-LNA modified oligonucleotides which can recruit RNAseH.

An additional object of the present invention is to provide Xylo-LNAs that can act as substrates for DNA and RNA polymerases thereby allowing the analogues to be either incorporated into a growing nucleic acid chain or to act as chain terminators.

A further object of the present invention is to provide Xylo-LNAs that can act as therapeutic agents. Many examples of therapeutic nucleoside analogues are known and similar derivatives of the nucleoside analogues disclosed herein can be synthesised using the procedures known from the literature (E. De Clercq, *J. Med. Chem.* 1995, 38, 2491; P. Herdewijn and E. De Clercq: Classical Antiviral Agents and Design of New Antiviral Agents. In: A Textbook of Drug Design and Development; Eds. P. Krogsgaard-Larsen, T. Liljefors and U. Madsen; Harwood Academic Publishers, Amsterdam, 1996, p. 425; I. K. Larsen: Anticancer Agents. In: A Textbook of Drug Design and Development; Eds. P. Krogsgaard-Larsen, T. Liljefors and U. Madsen; Harwood Academic Publishers, Amsterdam, 1996, p. 460).

Double-stranded RNA has been demonstrated to posses anti-viral activity and tumour suppressing activity (Sharp et al., *Eur. J. Biochem.* 1995, 230(1): 97–103, Lengyel-P. et al., *Proc. Natl. Acad. Sci. U.S.A.*, 1993, 90(13): 5893–5, and Laurent-Crawford et al., *AIDS Res. Hum. Retroviruses*, 1992, 8(2): 285–90). It is likely that double stranded LNAs may mimic the effect of therapeutically active double stranded RNAs and accordingly such double stranded LNAs has a potential as therapeutic drugs.

When used herein, the term "natural nucleic acid" refers to nucleic acids in the broadest sense, like for instance nucleic acids present in intact cells of any origin or vira or nucleic acids released from such sources by chemical or physical means or nucleic acids derived from such primary sources by way of amplification. The natural nucleic acid may be single, double or partly double stranded, and may be a relatively pure species or a mixture of different nucleic acids. It may also be a component of a crude biological sample comprising other nucleic acids and other cellular components. On the other hand, the term "synthetic nucleic acids" refers to any nucleic acid produced by chemical synthesis.

The present invention also provides the use of Xylo-LNA modified oligonucleotides in nucleic acid based therapeutic, diagnostics and molecular biology. The Xylo-LNA modified oligonucleotides can be used in the detection, identification, capture, characterisation, quantification and fragmentation of natural or synthetic nucleic acids, and as blocking agents for translation and transcription in vivo and in vitro. In many cases it will be of interest to attach various molecules to Xylo-LNA modified oligonucleotides. Such molecules may be attached to either end of the oligonucleotide or they may be attached at one or more internal positions. Alternatively, they may be attached to the oligonucleotide via spacers attached to the 5' or 3' end. Representative groups of such molecules are DNA intercalators, photochemically active groups, thermochemically active groups, chelating groups, reporter groups, and ligands. Generally all methods for labelling unmodified DNA and RNA oligonucleotides with these molecules can also be used to label Xylo-LNA modified oligonucleotides. Likewise, all methods used for detecting labelled oligonucleotides generally apply to the corresponding labelled, Xylo-LNA modified oligonucleotides.

Therapy

The term "strand displacement" relates to a process whereby an oligonucleotide binds to its complementary target sequence in a double stranded DNA or RNA so as to displace the other strand from said target strand.

In one aspect of the present invention, Xylo-LNA modified oligonucleotides capable of performing "strand displacement" are exploited in the development of novel pharmaceutical drugs based on the "antigene" approach. In contrast to oligonucleotides capable of making triple helices, such "strand displacement" oligonucleotides allow any sequence in a dsDNA to be targeted and at physiological ionic strength and pH.

The "strand displacing" oligonucleotides can also be used advantageously in the antisense approach in cases where the RNA target sequence is inaccessible due to intramolecular hydrogen bonds. Such intramolecular structures may occur in mRNAs and can cause significant problems when attempting to "shut down" the translation of the mRNA by the antisense approach.

Other classes of cellular RNAs, like for instance tRNAs, rRNAs snRNAs and scRNAs, comprise intramolecular structures that are important for their function. These classes of highly structured RNAs do not encode proteins but rather (in the form of RNA/protein particles) participate in a range of cellular functions such as mRNA splicing, polyadenylation, translation, editing, maintainance of chromosome end integrity, and so forth. Due to their high degree of structure, that impairs or even prevent normal oligonucleotides from hybridising efficiently, these classes of RNAs has so far not attracted interest as antisense targets.

The use of high affinity Xylo-LNA monomers should facilitate the construction of antisense probes of sufficient thermostability to hybridise effectively to such target RNAs. Therefore, in a preferred embodiment, Xylo-LNA is used to confer sufficient affinity to the oligonucleotide to allow it to hybridise to these RNA classes thereby modulating the qualitative and/or quantitative function of the particles in which the RNAs are found.

In some cases it may be advantageous to down-regulate the expression of a gene whereas in other cases it may be advantageous to activate it. As shown by Møllegaard et al. (Møllegaard, N. E.; Buchardt, O.; Egholm, M.; Nielsen, P. E. Proc. Natl. Acad. Sci. U.S.A. 1994, 91, 3892), oligomers capable of "strand displacement" can function as RNA transcriptional activators. In an aspect of the present invention, the LNAs capable of "strand displacement" are used to activate genes of therapeutic interest.

In chemotherapy of numerous viral infections and cancers, nucleosides and nucleoside analogues have proven effective. Xylo-LNA nucleosides are potentially useful as such nucleoside based drugs.

Various types of double-stranded RNAs inhibit the growth of several types of cancers. Duplexes involving fully Xylo-LNA modified oligonucleotide(s) are potentially useful as such double-stranded drugs.

The invention also concerns a pharmaceutical composition comprising a pharmaceutically active Xylo-LNA modified oligonucleotide or a pharmaceutically active Xylo-LNA monomer as defined above in combination with a pharmaceutically acceptable carrier.

Such compositions may be in a form adapted to oral, parenteral (intravenous, intraperitoneal), intramuscular, rectal, intranasal, dermal, vaginal, buccal, ocularly, or pulmonary administration, preferably in a form adapted to oral administration, and such compositions may be prepared in a manner well-known to the person skilled in the art, e.g. as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker.

Diagnostics

Several diagnostic and molecular biology procedures have been developed that utilise panels of different oligonucleotides to simultaneously analyse a target nucleic acid for the presence of a plethora of possible mutations. Typically, the oligonucleotide panels are immobilised in a predetermined pattern on a solid support such that the presence of a particular mutation in the target nucleic acid can be revealed by the position on the solid support where it hybridises. One important prerequisite for the successful use of panels of different oligonucleotides in the analysis of nucleic acids is that they are all specific for their particular target sequence under the single applied hybridisation condition. Since the affinity and specificity of standard oligonucleotides for their complementary target sequences depend heavily on their sequence and size this criteria has been difficult to fulfil so far.

In a preferred embodiment, therefore, Xylo-LNAs are used as a means to increase affinity and/or specificity of the probes and as a means to equalise the affinity of different oligonucleotides for their complementary sequences. As disclosed herein such affinity modulation can be accomplished by, e.g., replacing selected nucleosides in the oligonucleotide with a Xylo-LNA carrying a similar nucleobase.

In another preferred embodiment the high affinity and specificity of Xylo-LNA modified oligonucleotides is exploited in the sequence specific capture and purification of natural or synthetic nucleic acids. In one aspect, the natural or synthetic nucleic acids are contacted with the Xylo-LNA modified oligonucleotide immobilised on a solid surface. In this case hybridisation and capture occurs simultaneously. The captured nucleic acids may be, for instance, detected, characterised, quantified or amplified directly on the surface by a variety of methods well known in the art or it may be released from the surface, before such characterisation or amplification occurs, by subjecting the immobilised, modified oligonucleotide and captured nucleic acid to dehybridising conditions, such as for example heat or by using buffers of low ionic strength.

The solid support may be chosen from a wide range of polymer materials such as for instance CPG (controlled pore glass), polypropylene, polystyrene, polycarbonate or polyethylene and it may take a variety of forms such as for instance a tube, a micro-titer plate, a stick, a bead, a filter, etc. The Xylo-LNA modified oligonucleotide may be immobilised to the solid support via its 5' or 3' end (or via the terminus of linkers attached to the 5' or 3' end) by a variety of chemical or photochemical methods usually employed in the immobilisation of oligonucleotides or by non-covalent coupling such as for instance via binding of a biotinylated Xylo-LNA modified oligonucleotide to immobilised streptavidin. One preferred method for immobilising Xylo-LNA modified oligonucleotides on different solid supports is photochemical using a photochemically active anthraquinone covalently attached to the 5'- or 3'-end of the modified oligonucleotide (optionally via linkers) as described in (WO 96/31557). Thus, the present invention also provide a surface carrying an LNA modified oligonucleotide.

In another aspect the Xylo-LNA modified oligonucleotide carries a ligand covalently attached to either the 5'- or 3'-end. In this case the Xylo-LNA modified oligonucleotide is contacted with the natural or synthetic nucleic acids in solution whereafter the hybrids formed are captured onto a solid support carrying molecules that can specifically bind the ligand.

In still another aspect, Xylo-LNA modified oligonucleotides capable of performing "strand displacement" are used in the capture of natural and synthetic nucleic acids without prior denaturation. Such modified oligonucleotides are particularly useful in cases where the target sequence is difficult or impossible to access by normal oligonucleotides due to the rapid formation of stable intramolecular structures. Examples of nucleic acids comprising such structures are rRNA, tRNA, snRNA and scRNA.

In another preferred embodiment, Xylo-LNA modified oligonucleotides designed with the purpose of high specificity are used as primers in the sequencing of nucleic acids and as primers in any of the several well known amplification reactions, such as the PCR reaction. As shown herein, the design of the Xylo-LNA modified oligonucleotides determines whether it will sustain an exponential or linear target amplification. The products of the amplification reaction can be analysed by a variety of methods applicable to the analysis of amplification products generated with normal DNA primers. In the particular case where the Xylo-LNA modified oligonucleotide primers are designed to sustain a linear amplification the resulting amplicons will carry single stranded ends that can be targeted by complementary probes without denaturation. Such ends could for instance be used to capture amplicons by other complementary Xylo-LNA modified oligonucleotides attached to a solid surface.

In another aspect, Xylo-LNA modified oligonucleotides capable of "strand displacement" are used as primers in either linear or exponential amplification reactions. The use of such oligonucleotides is expected to enhance overall amplicon yields by effectively competing with amplicon re-hybridisation in the later stages of the amplification reaction. Demers, et al. (*Nucl. Acid Res.* 1995, Vol 23, 3050–3055) discloses the use of high-affinity, non-extendible oligomers as a means of increasing the overall yield of a PCR reaction. It is believed that the oligomers elicit these effects by interfering with amplicon re-hybridisation in the later stages of the PCR reaction. It is expected that Xylo-LNA modified oligonucleotides blocked at their 3' end will provide the same advantage. Blocking of the 3' end can be achieved in numerous ways like for instance by exchanging the 3' hydroxyl group with hydrogen or phosphate. Such 3' blocked Xylo-LNA modified oligonuclotides can also be used to selectively amplify closely related nucleic acid sequences in a way similar to that described by Yu et al. (*Biotechniques,* 1997, 23, 714–716).

In recent years, novel classes of probes that can be used in for example real-time detection of amplicons generated by target amplification reactions have been invented. One such class of probes have been termed "Molecular Beacons". These probes are synthesised as partly self-complementary oligonucleotides comprising a fluorophor at one end and a quencher molecule at the other end. When free in solution the probe folds up into a hairpin structure (guided by the self-complimentary regions) which positions the quencher in sufficient closeness to the fluorophor to quench its fluorescent signal. Upon hybridisation to its target nucleic acid, the hairpin opens thereby separating the fluorophor and quencher and giving off a fluorescent signal.

Another class of probes have been termed "Taqman probes". These probes also comprise a fluorophor and a quencher molecule. Contrary to the Molecular Beacons, however, the quenchers ability to quench the fluorescent signal from the fluorophor is maintained after hybridisation of the probe to its target sequence. Instead, the fluorescent signal is generated after hybridisation by physical detachment of either the quencher or fluorophor from the probe by the action of the 5'exonuxlease activity of a polymerase which has initiated synthesis from a primer located 5' to the binding site of the Taqman probe.

High affinity for the target site is an important feature in both types of probes and consequently such probes tends to be fairly large (typically 30 to 40 mers). As a result, significant problems are encountered in the production of high quality probes. In a preferred embodiment, therefore, LNA is used to improve production and subsequent performance of Taqman probes and Molecular Beacons by reducing their size whilst retaining the required affinity.

In a further aspect, Xylo-LNAs are used to construct new affinity pairs (either fully or partially modified oligonucleotides). The affinity constants can easily be adjusted over a wide range and a vast number of affinity pairs can be designed and synthesised. One part of the affinity pair can be attached to the molecule of interest (e.g. proteins, amplicons, enzymes, polysaccharides, antibodies, haptens, peptides, PNA, etc.) by standard methods, while the other part of the affinity pair can be attached to e.g. a solid support such as beads, membranes, micro-titer plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules mentioned above.

The principle of capturing a Xylo-LNA-tagged molecule by ways of interaction with another complementary Xylo-LNA oligonucleotide (either fully or partially modified) can be used to create an infinite number of novel affinity pairs.

In another preferred embodiment the high affinity and specificity of Xylo-LNA modified oligonucleotides are exploited in the construction of probes useful in in-situ hybridisation. For instance, Xylo-LNA could be used to reduce the size of traditional DNA probes while maintaining the required affinity thereby increasing the kinetics of the probe and its ability to penetrate the sample specimen.

In another preferred embodiment, Xylo-LNA modified oligonucleotides to be used in antisense therapeutics are designed with the dual purpose of high affinity and ability to recruit RNAseH. This can be achieved by, for instance, having Xylo-LNA segments flanking an unmodified central DNA segment.

The present invention also provides a kit for the isolation, purification, amplification, detection, identification, quantification, or capture of natural or synthetic nucleic acids, where the kit comprises a reaction body and one or more Xylo-LNA modified oligonucleotides (oligomer) as defined herein. The Xylo-LNA modified oligonucleotides are preferably immobilised onto said reaction body.

The present invention also provides a kit for the isolation, purification, amplification, detection, identification, quantification, or capture of natural or synthetic nucleic acids, where the kit comprises a reaction body and one or more Xylo-LNAs as defined herein. The Xylo-LNAs are preferably immobilised onto said reactions body (e.g. by using the immobilising techniques described above).

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtitre plate, a stick, or a multi-bladed stick.

The kits are typically accompanied by a written instruction sheet stating the optimal conditions for use of the kit.

Experimental

General

Reactions were conducted under an atmosphere of nitrogen when anhydrous solvents were used. Column chromatography was carried out on glass columns using Silica gel 60 (0.040–0.063 mm). After drying organic phases using $Na_2SO_4$, filtration was performed. Petroleum ether of distillation range 60–80° C. was used. Chemical shift values δ are in ppm relative to tetramethylsilane as internal reference ($^1H$ and $^{13}C$ NMR) and relative to 85% $H_3PO_4$ ($^{31}P$ NMR). Microanalyses were performed at The Microanalytical Laboratory, Department of Chemistry, University of Copenhagen.

Figure 2:
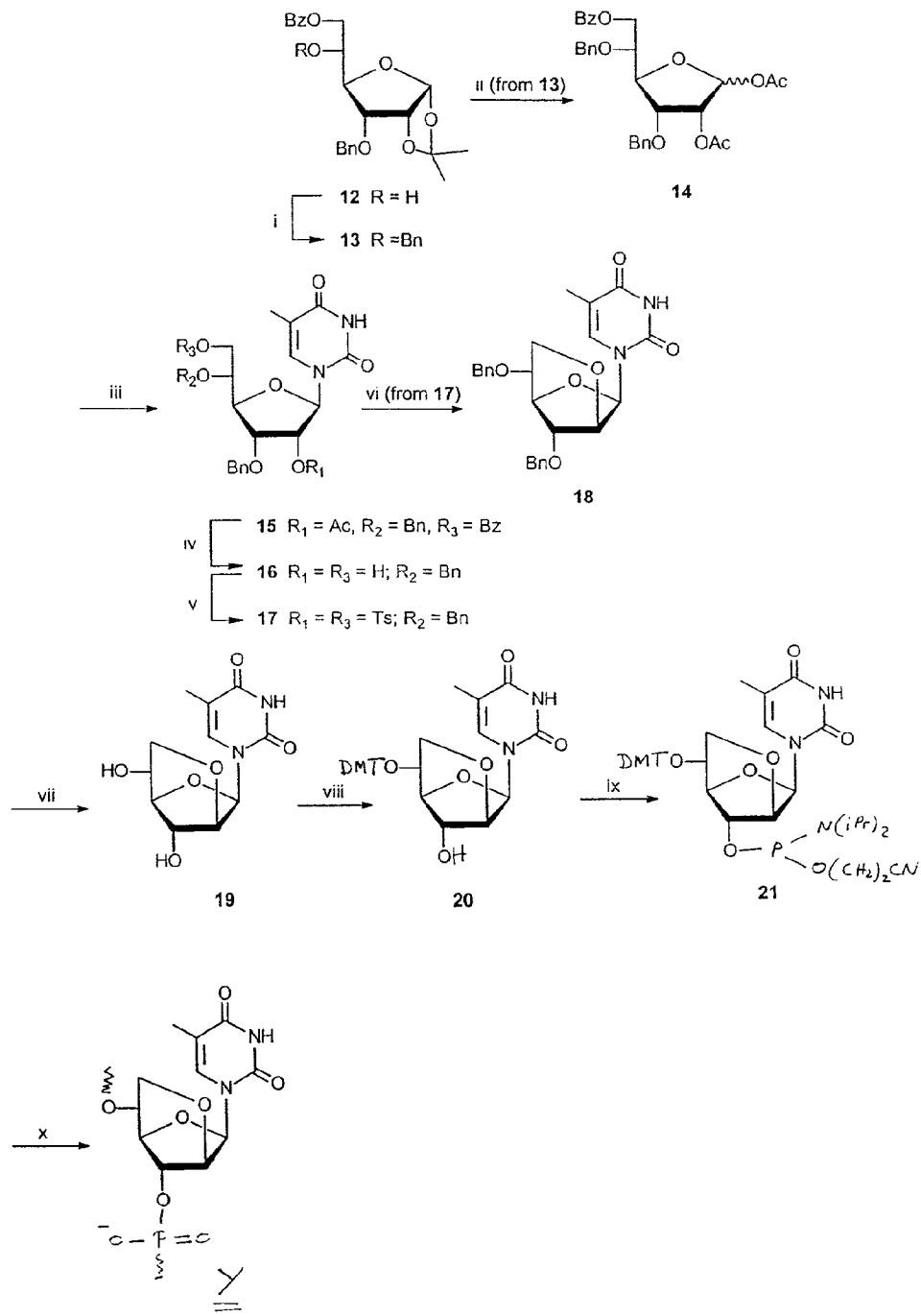

The specific descriptions below are accompanied by FIGS. 1–2 and Tables 1–2.

Preparation of Xylo-LNA Monomers

EXAMPLE 1

5-Benzoyl-4-C-benzoyloxymethyl-3-O-benzyl-1,2-O-isopropylidene-α-D-glucofuranose (2). To a stirred ice cold solution of 3-O-benzyl-4—C-hydroxymethyl-1,2-isopropylidene-α-D-glucofuranose (1)$^{26}$ (25.0 g, 0.096 mol) in anhydrous pyridine (60 cm$^3$) was added benzoyl chloride (4.1 cm$^3$, 0.035 mol). After stirring at room temperature for 4 h, the reaction mixture was cooled to 0° C., $H_2O$ (50 cm$^3$) was added, and the mixture was extracted with dichloromethane (100 cm$^3$×3). The combined organic phase was washed with saturated aqueous solutions of sodium hydrogen carbonate (30 cm$^3$×3) and brine (20 cm$^3$×3), dried ($Na_2SO_4$) and evaporated to dryness under reduced pressure. The residue was purified by silica gel column chromatography using first petroleum ether/dichloromethane (1:1, v/v) and then dichloromethane/methanol (99:1, v/v) as eluent to give furanose 2 (7.50 g, 90%) as a yellowish oil after evaporation of the solvents under reduced pressure.

$\delta_H$ (CDCl$_3$) 8.02–7.23 (15H, m), 6.08 (1H, d, J 4.2), 4.81–4.50 (7H, m), 4.22 (1H, d, J 1.0), 1.59 (3H, s), 1.37 (3H, s). $\delta_C$ (CDCl$_3$) 166.1, 165.8, 136.7, 133.1, 133.0, 129.9, 129.7, 129.6, 129.5, 128.5, 128.4, 128.3, 128.0, 127.9, 113.3, 105.4, 86.4, 85.1, 83.8, 72.3, 64.3, 63.8, 27.0, 26.4. FAB-MS m/z 521 [M+H]$^+$. Found (%) C, 69.1; H, 5.9; $C_{30}H_{32}O_8$ requires C, 69.2; H, 6.2.

EXAMPLE 2

5-O-Benzoyl-4-C-benzoyloxymethyl-3-O-benzyl-1,2-di-O-acetyl-D-glucofuranose (3). A solution of furanose 2 (7.40 g, 0.014 mol) in 80% acetic acid (60 cm$^3$) was stirred 9 h at 90° C. The mixture was evaporated to dryness under reduced pressure and the residue was coevaporated with toluene (10 cm$^3$×3) and dissolved in anhydrous pyridine (80 cm$^3$). Acetic anhydride (5.5 cm$^3$) was added and the solution was stirred for 46 h at room temperature. The mixture was evaporated to dryness under reduced pressure and the residue was coevaporated with toluene (10 cm$^3$×3) and dissolved in dichloromethane (150 cm$^3$). The solution was washed with saturated aqueous solutions of sodium hydrogen carbonate (30 cm$^3$×3) and brine (30 cm$^{3\times3}$), dried ($Na_2SO_4$) and concentrated under reduced pressure. The residue was purified by silica gel column chromatography using first petroleum ether/dichloromethane (1:1, v/v) and then dichloromethane/methanol (99:1, v/v) as eluent to give the anomeric mixture 3 (α:β=3:1, 7.33 g, 92%) as a clear oil after evaporation of the solvents under reduced pressure. This oil was used in the next step without further purification.

$\delta_C$ (CDCl$_3$) 169.4, 169.0, 165.8, 165.6, 137.0, 133.2, 133.1, 133.0, 129.6, 129.5, 129.2, 128.3, 127.8, 127.7, 127.4, 99.4, 92.3, 87.0, 83.2, 82.2, 80.7, 77.4, 76.9, 76.3, 73.2, 72.4, 20.9, 20.8, 20.6, 20.3. FAB-MS m/z 562 [M]$^+$.

EXAMPLE 3

1-(2-O-Acetyl-5-O-benzoyl-4-C-benzoyloxymethyl-3-O-benzyl-β-D-xylofuranosyl)thymine (4). To a stirred suspension of the anomeric mixture 3 (7.26 g, 0.013 mol) and thymine (3.25 g, 0.028 mol) in anhydrous acetonitrile (80 cm$^3$) was added N,O-bis(trimethylsilyl)acetamide (19.1 cm$^3$, 0.077 mol). The reaction mixture was stirred at 60° C. for 1 h and then cooled to 0° C. Trimethylsilyl triflate (4.1 cm$^3$, 0.023 mol) was added drop-wise during 10 min and the mixture was subsequently heated for 22 h under reflux. After cooling to room temperature, a saturated aqueous solution of sodium hydrogen carbonate (30 cm$^3$) was added and extraction was performed using dichloromethane (100 cm$^3$×3). The combined organic phase was washed with saturated aqueous solutions of sodium hydrogen carbonate (30 cm$^3$×3) and brine (50 cm$^3$×3), dried ($Na_2SO_4$) and concentrated under reduced pressure. The residue was purified by silica gel column chromatography using dichloromethane/methanol (0.5–2.0% methanol, v/v) as eluent to give nucleoside 4 (6.88 g, 85%) as a white solid material after evaporation of the solvents under reduced pressure.

$\delta_H$(CDCl$_3$) 8.97 (1H, br s), 8.04–7.23 (16H, m), 6.37 (1H, d, J 3.6), 5.42 (1H, t, J 3.1), 4.89–4.56 (6H, m), 4.22 (1H, d, J 2.6), 2.13 (3H, s), 1.74 (1H, d, J 0.8). $\delta_C$ (CDCl$_3$) 169.9, 166.0, 165.7, 163.4, 150.4, 136.2, 135.2, 133.5, 133.4, 129.8, 129.7, 129.6, 129.5, 129.0, 128.6, 128.4, 128.2, 112.0, 87.4, 86.0, 81.3, 80.3, 72.6, 63.1, 62.9, 20.8, 12.3. FAB-MS m/z 629 [M+H]$^+$. Found (%) C, 64.4; H, 4.9; N, 4.4; $C_{34}H_{32}N_2O_{10}$, 0.25$H_2O$ requires C, 64.5; H, 5.1; N, 4.4.

EXAMPLE 4

1-(3-O-Benzyl-4-C-hydroxymethyl-β-D-xylofuranosyl) thymine (5). To a stirred solution of nucleoside 4 (9.00 g, 0.014 mol) in methanol (130 cm$^3$) was added sodium methoxide (3.87 g, 0.0716 mol). The reaction mixture was stirred at room temperature for 4 h and then neutralised with dilute hydrochloric acid. The mixture was evaporated to dryness under reduced pressure followed by coevaporation using toluene (15 cm$^3$×3). The residue was purified by silica gel column chromatography using dichloromethane/methanol (4–1 5% methanol, v/v) as eluent to give nucleoside triol 5 (4.82 g, 89%) as a white solid material after evaporation of the solvents under reduced pressure.

$\delta_H$ (CD$_3$OD) 7.89 (1H, d, J 1.2), 7.40–7.24 (5H, m), 5.97 (1H, d, J 6.2), 4.83–4.65 (2H, m), 4.53 (1H, t, J 6.2), 4.21 (1H, d, J 6.2), 3.84 (1H, d, J 12.0), 3.63 (1H, d, J 12.0), 3.59 (2H, d, J 2.6), 1.82 (1H, d, J 1.1). $\delta_C$ (CD$_3$OD) 164.4, 150.9, 137.5, 136.6, 127.5, 127.0, 126.9, 109.8, 86.7, 86.4, 82.8, 78.0, 72.1, 62.3, 61.1, 10.5 (CH$_3$). FAB-MS m/z 379 [M+H]$^+$. Found (%) C, 56.2; H, 6.0; N, 7.0; $C_{18}H_{22}N_2O_7$, 0.25$H_2O$ requires C, 56.5; H, 5.9; N, 7.3.

EXAMPLE 5

1-(3-O-Benzyl-4-C-(p-Toluenesulphonyloxymethyl)β-D-xylofuranosyl)thymine (6). To a solution of nucleoside 5 (7.25 g, 0.0192 mol) in anhydrous pyridine (20 cm$^3$) and dichloromethane (70 cm$^3$) at −30° C. was drop-wise during 1.5 h added p-toluenesulphonyl chloride (4.38 g, 0.023 mol) dissolved in dichloromethane (8 cm$^3$).

The temperature was raised to 0° C. for 2 h, whereupon additional p-toluenesulphonyl chloride (1.80 g, 0.0094 mol) was added at −20° C. and the mixture was stirred for 12 h at −20° C. At that time further p-toluenesulphonyl chloride (0.736 g, 3.86 mmol) was added and stirring was continued at −20° C. for additional 24 h. The reaction mixture was diluted with dichloromethane (75 cm$^3$) and H$_2$O (75 cm$^3$) and extraction was performed with dichloromethane (75 cm$^3$×3). The combined organic phase was washed with saturated aqueous solutions of sodium hydrogen carbonate (30 cm$^3$×3) and brine (40 cm$^3$×3). The aqueous phase was extracted with ethyl acetate (30 cm$^3$×3), and these extracts were combined with the dichloromethane extracts, dried (Na$_2$SO$_4$) and evaporated to dryness under reduced pressure. The residue was purified by silica gel column chromatography using dichloromethane/methanol (1.5–3.5% methanol, v/v) as eluent to give nucleoside 6 (3.56 g, 35%) as a white solid material after evaporation of the solvents under reduced pressure.

$\delta_H$ (CDCl$_3$) 10.23 (1H, s), 7.78–7.26 (10H, m), 5.84 (1H,d, J 5.5), 4.84 (1H, d, J 11.5), 4.59 (1H, d, J 11.5), 4.53(1H, t, J 5.5), 4.19 (1H, d, J 5.6), 4.09 (1H, d, J 10.6), 4.03 (1H, d, J 10.6), 3.85 (1H, d, J 12.4), 3.67 (1H, d, J 12.4), 2.39 (3H, s), 1.78 (1H, d, J 0.6). $\delta_C$ (CDCl$_3$) 164.1, 151.5, 145.3, 137.0, 136.2, 132.3, 130.0, 128.6, 128.2, 128.0, 111.0, 88.5, 85.4, 83.8, 79.8, 73.2, 69.4, 63.0, 21.6, 12.5. FAB-MS m/z 533 [M +H]$^+$. Found (%) C, 56.7; H, 5.4; N, 4.9; C$_{25}$H$_{28}$N$_2$O$_9$S requires C, 56.4; H, 5.3; N, 5.2.

EXAMPLE 6

1-(3-O-Benzyl-5-O-(4,4'-dimethoxytrityl)-4-C-(p-toluenesulphonyloxymethyl)-β-D-xylofuranosyl)thymine (7). To a solution of nucleoside 6 (3.66 g, 6.88 mmol) in anhydrous pyridine (25 cm$^3$) was added N,N-(dimethylamino)pyridine (0.84 g, 6.81 mmol) and 4,4'-dimethoxytrityl chloride (3.5 g, 13.2 mmol) and the mixture was stirred for 23 h at room temperature. Additional N,N-(dimethylamino)pyridine (0.250 g, 2.06 mmol) and 4,4'-dimethoxytrityl chloride (0.700 g, 2.06 mmol) was added, and stirring was continued for 36 h at room temperature. Ice cold H$_2$O (50 cm$^3$) was added and the reaction mixture was diluted with dichloromethane (150 cm$^3$). The organic phase was separated and washed with saturated aqueous solutions of sodium hydrogen carbonate (25 cm$^3$×3) and brine (40 cm$^3$×3), dried (Na$_2$SO$_4$) and evaporated to dryness under reduced pressure. The residue was purified by silica gel column chromatography using dichloromethane/methanol/pyridine (0.75–1.5% methanol; 0.5% pyridine, v/v/v) as eluent to afford nucleoside 7 (4.28 g, 75%) as a white solid material after evaporation of the solvents under reduced pressure.

$\delta_H$ (CDCl$_3$) 9.40 (1H, s), 7.72–6.68 (23H, m), 5.77 (1H, d, J 4.2), 4.86 (1H, d, J 11.3), 4.49–4.43 (2H, m), 4.23–4.12 (3H, m), 3.76 (3H, s), 3.75 (3H, s), 3.45 (1H, d, J 10.2), 3.17 (1H, d, J 10.2), 2.37 (3H, s),1.44 (1H, s). $\delta_C$ (CDCl$_3$) 163.7, 158.5, 151.0, 144.9, 144.4, 137.1, 135.8, 135.2, 135.0, 132.5, 130.1, 129.8, 128.3, 128.0, 127.8, 127.7, 126.9, 113.1, 110.0, 90.2, 87.1, 86.4, 83.3, 79.9, 72.9, 68.7, 62.2, 55.2, 21.6, 12.0. FAB-MS m/z 835 [M+H]$^+$. Found (%) C, 66.0; H, 5.7; N, 3.3; C$_{46}$H$_{46}$N$_2$O$_{11}$S requires C, 66.1; H, 5.5; N, 3.4.

EXAMPLE 7

(1R,3R,4R,7R)-7-Benzyloxy-1-(4,4'-dimethoxytrityloxymethyl)-3-(thymin-1-yl)-2,5-dioxabicyclo[2.2.1]heptane (8). To a solution of nucleoside 7 (4.22 g, 5.06 mmol) in anhydrous DMF (25 cm$^3$) at 0° C. was added a 60% suspension of sodium hydride in mineral oil (w/w, 0.607 g, 1 5.7 mmol, added in four portions during 20 min) and the reaction mixture was stirred at room temperature for 25 h, cooled to 0° C. and diluted with dichloromethane/pyridine (100 cm$^3$, 99.5:0.5, v/v). A saturated aqueous solution of sodium hydrogen carbonate (120 cm$^3$) was added whereupon extraction was performed using dichloromethane (75 cm$^3$×2). The combined organic phase was washed with saturated aqueous solutions of sodium hydrogen carbonate (60 cm$^3$×3) and brine (40 cm$^3$×3), dried (Na$_2$SO$_4$) and evaporated to dryness under reduced pressure. The residue was purified by silica gel column chromatography using dichloromethane/methanol/pyridine (0.5–1.5% methanol; 0.5% pyridine, v/v/v) as eluent yielding nucleoside 8 (3.2 g, 96%) as a white solid material after evaporation of the solvents under reduced pressure.

$\delta_H$ (CDCl$_3$) 13.24 (1H, s, NH), 7.70–7.19 (19H, m, Bn, DMT, 6-H), 6.15 (1H, s, 1'-H), 4.98 (1H, s, 2'-H), 4.55 (1H, d, J 11.2, Bn), 4.42 (1H, d, J 11.2, Bn), 4.40 (1H, s, 3'-H), 4.34 (1H, d, J 8.0, 1"-H$_a$), 4.17 (1H, d, J 8.0, 1"-H$_b$), 3.94 (2H, s, 5'-H), 3.67 (3H, s, OCH$_3$), 3.64 (3H, s, OCH$_3$), 1.75 (1H, d, J 0.7, CH$_3$). $\delta_C$ (CDCl$_3$) 165.0 (C-4), 159.2, 151.5, 145.5, 137.4, 136.6, 136.0, 130.6, 128.7, 128.6, 128.4, 128.3, 127.3, 113.8, 108.1, 89.3, 88.6, 86.7, 80.6, 77.0, 73.8, 73.0, 59.8, 55.2, 12.7. FAB-MS m/z 663 [M+H]$^+$. Found (%) C, 70.4; H, 5.8; N, 4.0; C$_{39}$H$_{38}$N$_2$O$_8$ requires C, 70.7; H, 5.7; N, 4.2.

EXAMPLE 8

(1S,3R,4R,7R)-7-hydroxy-1-hydroxymethyl-3-(thymin-1-yl)-2,5-dioxabicyclo [2.2.1]heptane (9). Nucleoside 8 (3.09 g, 4.66 mmol) was dissolved in methanol (40 cm$^3$) and 10% palladium on carbon (3 g, suspended in methanol (20 cm$^3$)) was added. The mixture was degassed and stirred under an atmosphere of hydrogen. After 26 h, the mixture was filtered (silica gel, washed with dichloromethane/methanol (700 cm$^3$; 1:3, v/v)) and the volume of the filtrate was concentrated to 25% of its initial volume. After repeated filtration, the filtrate was evaporated to dryness under reduced pressure and the residue was subjected to column chromatography on silica gel using dichloromethane/methanol (5–12% methanol, v/v) as eluent furnishing nucleoside 9 (1.03 g, 82%) as a white solid material after evaporation of the solvents under reduced pressure.

$\delta_H$ (CD$_3$OD) 7.73 (1H, d, J 1.1, 6-H), 5.56 (1H, s, 1'-H), 4.32 (1H, d, J 2.2, 2'-H), 4.21 (1H, d, J 2.2, 3'-H), 4.06 (1H, d, J 8.2, 1"-H$_a$), 4.01 (2H, s, 5'-H), 3.86 (1H, d, J 8.2, 1"-H$^b$), 1.85 (1H, d, J 1.1, CH$_3$). $\delta_C$ (CD$_3$OD) 166.8, 139.4, 108.4, 91.0, 90.3, 79.6, 74,5, 70.0, 59.0, 12.6. FAB-MS m/z 271 [M+H]$^+$. Found (%) C, 47.8; H, 5.5; N, 9.5; C$_{11}$H$_{14}$N$_2$O$_6$, 0.5H$_2$O requires C, 47.3; H, 5.4; N, 10.0.

EXAMPLE 9

(1R,3R,4R,7R)-1-(4,4'-dimethoxytrityloxymethyl )-7-hydroxy-3-(thymin-1-yl)-2,5-dioxabicyclo[2.2.1]heptane (10).

To a stirred solution of nucleoside 9 (0.500 g, 1.85 mmol) in anhydrous pyridine (10 cm$^3$) was added 4,4'-dimethoxytrityl chloride (0.941 g, 2.78 mmol) and the mixture was stirred for 25 h at room temperature for 25 h after which additional 4,4'-dimethoxytrityl chloride (0.062 g, 0.18 mmol) was added and stirring at room temperature was continued for another 21 h. A saturated aqueous solution of sodium hydrogen carbonate (50 cm$^3$) was added and extraction was performed using dichloromethane (3×25 cm$^3$). The combined organic phase was washed with saturated aqueous solutions of sodium hydrogen carbonate (3×20 cm$^3$) and brine (3×25 cm$^3$), dried (Na$_2$SO$_4$) and evaporated to dryness under reduced pressure. The residue was purified by silica gel column chromatography using dichloromethane/methanol/pyridine (1–4% methanol, 0.5% pyridine, v/v/v) as eluent to give nucleoside 10 (0.53 g, 50%) as a white solid material after evaporation of the solvents under reduced pressure (0.307 g, 28.9%).

$\delta_H$ (CDCl$_3$) 9.30 (1H, s, NH), 7.69 (1H, d, J 1.1, 6-H), 7.46–6.84 (13H, m, DMT), 5.74 (1H, s,1 '-H), 4.60 (1H, d, J 2.0, 3'-H), 3.91 (2H, s, 5'-H), 3.80 (6H, s, OCH$_3$), 3.68 (1H, d, J 10.6, 1"-H$_a$), 3.61 (1H, d, J 10.6, 1"-H$_b$), 1.79 (1H, d, J 1.1, CH$_3$). $\delta_C$ (C$_5$H$_5$N) 165.2, 159.3, 151.7, 145.8, 137.6, 136.4, 136.2, 130.7, 128.7, 128.4, 127.4, 124.3, 113.8, 107.6, 90.6, 86.9, 86.7, 79.0, 74.3, 61.2, 55.2, 13.0 (CH$_3$). FAB-MS m/z 573 [M+H]$^+$. Found (%) C, 66.6; H, 5.7; N, 4.7; C$_{32}$H$_{32}$N$_2$O$_8$,0.25H$_2$O requires C, 66.6; H, 5.7; N, 4.9.

EXAMPLE 10

(1R,3R,4R,7R)-7-(2-Cyanoethoxy(diisopropylamino) phosphinoxy)-1-(4,4'-dimethoxytrityloxymethyl)-3-(thymin-1-yl)-2,5-dioxabicyclo [2.2.1]heptane (11). To a stirred solution of nucleoside 10 (0.487 g, 0.851 mmol) in anhydrous dichloromethane (10 cm$^3$) was added N,N-diisopropylethylamine (0.600 cm$^3$, 3.41 mmol) and 2-cyanoethyl N,N-diisopropylphosphoramidochloridite (0.230 cm$^3$, 1.02 mmol) and the mixture was stirred for 21 h at room temperature. Additional N,N-diisopropylethylamine (0.150 cm$^3$, 0.851 mmol) and 2-cyanoethyl N,N-diisopropylphosphoramidochloridite (0.100 cm$^3$, 0.426 mmol) was added and stirring was continued for another 22 h at room temperature. After cooling the reaction mixture to 0° C. a saturated aqueous solution of sodium hydrogen carbonate (10 cm$^3$) was added and extraction was performed using dichloromethane (3×15 cm$^3$). The combined organic phase was washed with saturated aqueous solutions of sodium hydrogen carbonate (3×15 cm$^3$) and brine (3×15 cm$^3$), dried (Na$_2$SO$_4$) and evaporated to dryness under reduced pressure. The residue was purified by silica gel column chromatography using dichloromethane/methanol/pyridine (0.5–1.0% methanol, 0.5% pyridine, v/v/v) as eluent to give crude amidite as a yellowish oil after evaporation of the solvents under reduced pressure. The residue was dissolved in anhydrous dichloromethane (2 cm$^3$) and precipitated by dropwise addition of this solution into vigorously stirred petroleum ether (60–80° C., 30 cm$^3$, −30° C.) to give amidite 11 (0.354 g, 51%) as a white solid material after filtration and drying.

$\delta_P$ (CD$_3$CN) 154.0, 151.8.

Preparation of LNA Oligonucleotides

EXAMPLE 11

Synthesis of unmodified oligonucleotides and oligonucleotides comprising Xylo-LNA of the formula X. Xylo-LNA and reference oligonucleotides were prepared on a Biosearch 8750 DNA Synthesizer. Coupling of amidite 11 was performed by "hand coupling" (premixing amidite and the activator in acetonitrile in a syringe; then flushing the column reactor approximately twice every minute throughout the coupling time applied; CPG solid supports). In optimisation experiments, the xylo-LNA oligomer 5'-XT$_6$ was synthesised using amidite 11 and as activator either 1H-tetrazole (0.26 M, 10 min coupling: 15% yield; 30 min coupling: 31% yield), 4,5-dicyanoimidazole (0.27 M; 30 min coupling: 71% yield) or pyridine hydrochloride (0.27 M; 30 min coupling: 100% yield). Synthesis of the xylo-LNAs were accomplished using pyridine hydrochloride as activator (10–30 min coupling time; step-wise coupling yields for amidite 11 were 86–95%). During synthesis of 5'-X$_{13}$T two additions of amidite/activator solution was performed before capping any unreacted 5'-hydroxyl functionality. The unmodified 2'-deoxynucleoside 2-cyanoethyl N,N-diisopropylphosphoramidites were coupled by use of the standard DNA-program of the synthesiser except for the couplings immediately following an X monomer which were conducted according to the RNA program of the synthesiser. After completion of the sequences, deprotection using concentrated ammonia in methanol (32% (w/w), room temperature, 12 h of 5'-O-DMT-ON oligonucleotides and subsequently reversed phase purification (commercially available disposable cartridges (Cruachem); procedure includes detritylation) yielded the final oligomeric products. However, for all unmodified oligonucleotides and the xylo-LNA comprising only one X monomer the 5'-O-DMT group was removed on the synthesiser immediately after completion of the sequences. Subsequent treatment with concentrated ammonia in methanol (32% (w/w), 12 h, 55° C.) and ethanol precipitation afforded the product oligomers. Capillary gel electrophoresis was used to analyse the purity of the synthesised xylo-LNAs. In addition, the sequence 3'-X$_{10}$$^{5'}$-$^{5'}$C-3' was synthesised using the regioisomeric 3'—O—DMT—5'-O-phosphitylated amidite.

Hybridisation Data

EXAMPLE 12

Thermostability of oligonucleotides comprising monomer X. The thermostability of the Xylo-LNA modified oligonucleotides were determined spectrophotometrically using a spectrophotometer equipped with a thermoregulated Peltier element. Hybridisation mixtures of 1 ml were prepared using a medium salt buffer solution (10 mM Na$_2$HPO$_4$, pH 7.0, 100 mM NaCl, 0.1 mM EDTA) and equimolar (1 µM or 1.5 µM) amounts of the different Xylo-LNA modified oligonucleotides and their complementary DNA or RNA oligonucleotides. Identical hybridisation mixtures using the unmodified oligonucleotides were prepared as references. The absorbance at 260 nm was recorded while the temperature was raised linearly from 10–90° C. (1° C./min). The melting temperatures (T$_m$ values) were obtained as the maxima (+/−1° C.) of first derivative of the melting curves. Table 1 summarises the results (Xylo-LNAs are marked with bold). FIG. 1 illustrates the monomeric Xylo-LNAs used.

From table 1 it can be seen that incorporation of a single xylo-LNA monomer X into an oligonucleotide sequence (A), or more Xylo-LNAs X alternating with unmodified monomers (B), induces a pronounced decrease in the thermal stability of duplexes formed with the complementary single stranded DNA and RNA. Surprisingly, consecutive incorporation of the monomer X into an oligonucleotide sequence, affording the fully modified Xylo-LNA oligonucleotide D, showed a remarkably increase in the thermal stability of duplexes formed with the complementary DNA and RNA. The remarkably strong hybridisation property observed for D indicates that high-affinity targeting of nucleic acids using xylo-LNA modified oligonucleotides requires a continuous stretch of xylo-LNA monomers. This fact reflects the structural characteristics of xylose configurated monomers with the stereochemistry around C-3' being inverted compared to the natural ribo-NAs. The orientation of the two strands in complexes D:F and D:G can be anti-parallel as for the corresponding unmodified duplexes, or parallel.

Preparation of 2'-O,5'-C-methylene LNA Monomers

EXAMPLE 13

6-O-Benzoyl-3,5-di-O-benzyl-1,2-di-O-isopropylidene-α-D-allofuranose (13). To a stirred solution of furanose 12 (4.60 g, 11.1 mmol) in anhydrous DMF (20 cm$^3$) at 0° C. was added a 60% suspension of sodium hydride in mineral oil (w/w, 0.67 g, 16.7 mmol, added in four portions during 20 min). After stirring for 30 min, benzyl bromide (1.99 cm$^3$, 16.7 mmol) was added and stirring was continued for 2 h at room temperature. The mixture was cooled to 0° C., H$_2$O (30 cm$^3$) was added and extraction was performed using dichloromethane (50 cm$^3$×3). The combined organic phase was washed with saturated aqueous solutions of sodium hydrogen carbonate (30 cm$^3$×3) and brine (20 cm$^3$×3), dried (Na$_2$SO$_4$) and evaporated to dryness under reduced pressure. The residue was purified by silica gel column chromatography using ethyl acetate/petroleum ether (1:9, v/v) as eluent to give furanose 13 as yellowish oil (5.0 g, 90%) after evaporation of the solvents under reduced pressure. This oil was used in the next step without further purification.

$\delta_H$ (CDCl$_3$) 7.99 (2H, m), 7.58–7.21 (13H, m), 5.77 (1H, d, J 3.6), 4.77–4.00 (10H, m), 1.59 (3H, s), 1.35 (3H, s). $\delta_C$ (CDCl$_3$) 166.24, 138.4, 137.41, 133.0 130.1, 129.7, 128.4, 128.3, 128.2, 128.1, 127.9, 127.8, 127.7, 127.5, 113.1, 102.2, 79.2, 77.6, 76.5, 76.3, 73.7, 72.2, 64.3, 27.0, 26.6. FAB-MS m/z 505 [M+H]$^+$.

EXAMPLE 14

6-O-Benzoyl-1,2-di-O-acetyl-3,5-di-O-benzyl-D-allofuranose (14). A solution of furanose 13 (5.00 g, 9.92 mmol) in 80% acetic acid (75 cm$^3$) was stirred for 10 h at 80° C. The solvent was removed under reduced pressure and the residue was coevaporated with toluene (10 cm$^3$×3) and dissolved in a mixture of anhydrous pyridine (30 cm$^3$) and dichloromethane (30 cm$^3$). Acetic anhydride (5.0 cm$^3$) was added and the solution was stirred for 20 h at room temperature. The mixture was evaporated to dryness under reduced pressure and the residue was dissolved in dichloromethane (150 cm$^3$), washed with saturated aqueous solutions of sodium hydrogen carbonate (60 cm$^3$) and brine (30 cm$^3$), dried (Na$_2$SO$_4$) and evaporated to dryness under reduced pressure. The residue was purified by silica gel column chromatography using petroleum ether/dichloromethane (1:1, v/v) as eluent affording the anomeric mixture 14 as a clear oil (4.50 g, 74%) after evaporation of the solvents under reduced pressure. This oil was used in the next step without further purification.

$\delta_C$ (CDCl$_3$) 169.9, 169.2, 165.8, 166.2, 138.6, 137.0, 133.2, 133.1, 133.0, 129.9, 129.7, 128.5, 128.4, 128.3, 128.2, 128.1, 128.0, 127.9, 127.8, 127.7, 127.6, 127.5, 127.4, 98.6, 94.3, 84.7, 82.3, 82.0, 77.7, 76.5, 76.4, 76.3, 74.7, 74.1, 73.9, 73.3, 73.1, 72.8, 71.8, 70.0, 63.8, 63.2, 21.2, 20.8, 20.8, 20.6. FAB-MS m/z 547 [M−H]$^+$.

EXAMPLE 15

1-(2-O-acetyl-6-O-benzoyl-3,5-di-O-benzyl-β-D-allofuranosyl)thymine (15). To a stirred suspension of the anomeric mixture 14 (4.50 g, 8.21 mmol) and thymine (1.55 g, 12.31 mmol) in anhydrous acetonitrile (50 cm$^3$) was added N,O-bis(trimethylsilyl)-acetamide (12.2 cm$^3$, 49.3 mmol). The reaction mixture was stirred at 60° C. for 1 h and then cooled to 0° C. Trimethylsilyl triflate (2.97 cm$^3$, 16.4 mmol) was added dropwise during 10 min and the mixture was heated for 2 h under reflux. The reaction mixture was allowed to cool to room temperature and the volume was reduced by 50% under reduced pressure. After cooling to 0° C., a saturated aqueous solution of sodium hydrogen carbonate (100 cm$^3$) was added and extraction was performed with dichloromethane (2×50 cm$^3$). The combined organic phase was washed with brine (50 cm$^3$), dried (Na$_2$SO$_4$) and evaporated to dryness under reduced pressure. The residue was purified by silica gel column chromatography using dichloromethane/methanol (99.5:0.5, v/v) as eluent to give nucleoside 15 as white solid material (4.06 g, 81%) after evaporation of the solvents under reduced pressure.

$\delta_H$ (CDCl$_3$) 8.74 (1H, br s), 8.01 (2H, m), 7.61–7.11 (14H, m), 6.09 (1H, d, J 5.3), 5.32 (1H, m), 4.86 (1H, d, J 11.7), 4.65 (1H, d, J 11.7), 4.55–4.10 (7H, m), 2.10 (3H, s), 1.59 (3H, s). $\delta_C$ (CDCl$_3$) 170.0, 166.1 166.0, 163.4, 150.2, 137.4, 137.0, 135.7, 133.3, 129.7, 128.6, 128.5, 128.1, 128.0, 127.9, 127.7, 127.3, 126.9, 111.7, 87.6, 82.6, 76.7, 75.3, 73.7, 73.1, 73.0, 63.3, 20.7, 12.0. FAB-MS m/z 615 [M+H]$^+$. Found (%) C, 66.4; H, 5.6; N, 4.4; C$_{34}$H$_{34}$N$_2$O$_9$ requires C, 66.4; H, 5.6; N, 4.6.

EXAMPLE 16

1-(3,5-di-O-benzyl-β-D-allofuranosyl)thymine (16). To a stirred solution of nucleoside 15 (3.00 g, 4.88 mmol) in methanol (50 cm$^3$) was added sodium methoxide (0.79 g, 14.7 mmol). The reaction mixture was stirred for 14 h at room temperature and subsequently neutralised with dilute hydrochloric acid (5 cm$^3$) whereupon ice-cold H$_2$O (50 cm$^3$) was added. The resulting mixture was extracted using ethyl acetate (3×100 cm$^3$) and the combined organic phase was evaporated to dryness under reduced pressure. The residue was purified by silica gel column chromatography using dichloromethane/methanol (98.5:1.5, v/v) as eluent to give nucleoside 16 as white solid material (2.00 g, 88%) after evaporation of the solvents under reduced pressure.

$\delta_H$ (CDCl$_3$) 9.39 (1H, br s), 7.38–7.15 (11H, m), 5.80 (1H, d, J 4.6), 4.80–3.55 (10H, m), 1.59 (3H, s). $\delta_C$ (CDCl$_3$) 163.7, 150.8, 137.7, 136.8, 136.3, 128.7, 128.4, 128.2, 128.0, 127.3, 111.4, 90.4, 82.7, 78.8, 76.5, 72.9, 72.5, 72.4, 60.7, 12.0. FAB-MS m/z 469 [M+H]$^+$. Found (%) C, 64.4; H, 6.1; N, 5.5; C$_{25}$H$_{28}$N$_2$O$_7$ requires C, 64.1; H, 6.0; N, 6.0.

EXAMPLE 17

1-(3,5-di-O-benzyl-2,6-di-O-(p-toluenesulphonyl)-β-D-allofuranosyl)thymine (17). To a stirred solution of nucleoside 16 (0.60 g, 1.28 mmol) in dichloromethane (70 cm$^3$) at room temperature was added 4—N,N-(dimethylamino)pyridine (0.63g, 5.12 mmol) and p-toluenesulphonyl chloride (0.73 g, 3.84 mmol). After stirring for 3 h, ice-cold H$_2$O (50 cm$^3$) was added and extraction was performed using dichloromethane (3×75 cm$^3$). The combined organic phase was dried (Na$_2$SO$_4$) and evaporated to dryness under reduced pressure. The residue was purified by silica gel column chromatography using dichloromethane/methanol (99.5:0.5, v/v) as eluent to give nucleoside 17 as white solid material (0.71 g, 71%) after evaporation of the solvents under reduced pressure.

$\delta_H$ (CDCl$_3$) 8.83 (1H, br s), 7.73–7.12 (18H, m), 6.58 (1H, d, J 1.2), 5.88 (1H, d, J 6.9), 5.0 (1H, m), 4.73–3.82 (9H, m), 2.40 (3H, s), 2.35 (3H, s),1.48 (3H, d, J 0.9). $\delta_C$ (CDCl$_3$) 163.1, 149.8, 145.8, 145.2, 137.1, 137.0, 135.6, 132.4, 132.3, 130.0, 128.7, 128.5, 128.3, 128.1, 128.0, 127.8, 127.2, 111.4, 86.9, 83.1, 77.7, 75.3, 73.1, 72.5, 67.4, 21.7, 11.9. FAB-MS m/z 777 [M+H]$^+$. Found (%) C, 60.6; H, 5.2; N, 3.5; $C_{39}H_{40}N_2O_{11}S_2$ requires C, 60.3; H, 5.2; N, 3.6.

EXAMPLE 18

(1S,4R,5R,7R,8R)-4,8-Dibenzyloxy-7-(thymin-1-yl)-2,6-dioxabicyclo[3.2.1]octane (18).

To a stirred solution of nucleoside 17 (0.63 g, 0.81 mmol) in a mixture of ethanol and H$_2$O (40 cm$^3$, 1:1, v/v) at room temperature was added an aqueous solution of sodium hydroxide (1M, 7 cm$^3$). The resulting mixture was heated under reflux for 16 h and then neutralised by addition of dilute hydrochloric acid (10 cm$^3$). The volume of the mixture was reduced to 50% and extraction was performed using dichloromethane (50 cm$^3$×3). The combined organic phase was dried (Na$_2$SO$_4$) and evaporated to dryness under reduced pressure. The residue was purified by silica gel column chromatography using dichloromethane/methanol (99:1,v/v) as eluent to give nucleoside 18 as a white solid material (0.40 g, 93%) after evaporation of the solvents under reduced pressure.

$\delta_H$ (CDCl$_3$) 8.69 (1H, br s), 7.90 (1H, d, J 1.1), 7.39–7.25 (10H, m), 5.85 (1H, d, J 2.2), 4.78–4.47 (6H, m), 3.87–3.38 (4H, m), 1.87 (3H, s). $\delta_C$ (CDCl$_3$) 163.9, 149.9, 137.3, 137.1, 136.8, 128.6, 128.5, 128.2, 128.1, 127.8, 127.7, 109.4, 88.6, 79.9, 79.7, 74.5, 73.5, 71.4, 70.8, 65.0, 12.5. FAB-MS m/z 451 [M+H]$^+$. Found (%) C, 66.3; H, 5.7; N, 6.1; $C_{25}H_{26}N_2O_6$ requires C, 66.7; H, 5.8; N, 6.2.

EXAMPLE 19

(1S,4R,5R,7R,8R)-4,8-Dihydroxy-7-(thymin-1-yl)-2,6-dioxabicyclo[3.2.1]octane (19). Nucleoside 18 (0.27 g, 0.60 mmol) was dissolved in absolute ethanol (20 cm$^3$) and 20% palladium hydroxide on carbon (0.25 g) was added. The mixture was degassed and placed under an atmosphere of hydrogen. After stirring for 26 h the catalyst was filtered off (silica gel, washed with methanol, 400 cm$^3$) and the filtrate was concentrated to dryness under reduced pressure. The residue was subjected to column chromatography on silica gel using dichloromethane/methanol (94:6, v/v) as eluent to give nucleoside 19 as white solid material (0.16 g, 98%) after evaporation of the solvents under reduced pressure.

$\delta_H$ (CD$_3$OD) 8.06 (1H, d, J 1.2, 6-H), 5.57 (1H, d, J 2.3, 1'-H), 4.5 (1H, m, 2'-H), 4.42 (1H, s, 4'-H), 4.03 (1H, m, 3'-H), 3.93–3.80 (2H, m, 5'-H, 6'-H$_a$), 3.21 (1H, m, 6'-H$_b$), 1.91 (3H, d, J 1.2, CH$_3$). $\delta_C$ (CD$_3$OD) 166.8 (C-4), 152.0 (C-2), 139.4 (C-6), 110.2 (C-5), 90.2 (C-1'), 87.3 (C-4'), 77.0 (C-2'), 74.7 (C-3'), 68.5 (C-5'), 67.4 (C-6'), 12.5 (CH$_3$). FAB-MS m/z 271 [M+H]$^+$.

EXAMPLE 20

(1S,4R,5S,7R,8R)-4-(4,4'-Dimethoxytrityloxy)-8-hydroxy-7-(thymin-1-yl)-2,6-dioxabicyclo[3.2.1]octane (20).

For the purpose of incorporating nucleoside 19 into an oligonucleotide, the phosphor-amidite derivative 21 was synthesised utilising standard conditions essentially as described above for synthesis of amidite 11 from nucleoside 9 via 5'-O-DMT derivative 10. Thus reaction with DMTCI afforded a mixture of the 5'-O-DMT-(20) and the 3'-O-DMT protected compounds (isolated in 16% and 17% yield, respectively) after reaction with DMTCI and DMAP in dichloromethane.

EXAMPLE 21

(1S,4R,5R,7R,8R)-8-(2-Cyanoethoxy(diisopropylamino) phosphinoxy)-4-(4,4'-di-methoxytrityloxy)-7-(thymin-1-yl)-2,6-dioxabicyclo[3.2.1]octane (21).

The 5'-O-DMT regioisomer 20 was converted to the 3'-O-phosphoramidite derivative 21 in 51% yield by standard phosphitylation (see above for synthesis of 11; see caption Scheme 2). $\delta_P$ (CD$_3$CN) 150.0, 148.9.

Analogously, the 3'-O-DMT regioisomer was transformed into the 5'-O-phosphitylated derivative. $\delta_P$ (CD$_3$CN) 150.1, 148.8.

Preparation of LNA Modified Oligonucleotides

EXAMPLE 22

Synthesis of oligonucleotides containing the 2'-O,5'-C-methylene linked monomer Y.

Oligonucleotides containing the 2'-O,5'-C-methylene linked monomer Y were prepared using the oligomerisation, deblocking and purification methods described above for synthesis of xylo-LNA. Either the amidite 21 or the 3'-O-DMT regioisomeric amidite were used in combination with unmodified amidites. The coupling yields for amidite 21, its regioisomer as well as unmodified amidites were above 95%.

Hybridisation Data

EXAMPLE 23

Thermostability of oligonucleotides comprising monomer Y. The thermostability of the 2'-O,5'-C-methylene-LNA modified oligonucleotides were determined as described above.

From table 2 it can be seen that incorporation of a single 2'-O,5'-C-methylene-LNA monomer Y into an oligonucleotide sequence (H), or consecutive introduction of four Y monomers (I), induces a pronounced decrease in the thermal stability of duplexes formed with the complementary single stranded DNA and RNA.

TABLE 1

| Sequence[a] | | $T_m$ (° C.)[b] | $T_m$ (° C.)[c] |
|---|---|---|---|
| 5'-T$_7$XT$_6$ | (A) | 19 | 24 |
| 5'-T$_3$(XT)$_4$T$_3$ | (B) | no $T_m$ | 9 |
| 5'-T$_5$X$_4$T$_5$ | (C) | 21 | 15 |
| 5'-X$_9$T | (D') | 48 | 57 |
| 5'-X$_{13}$T | (D) | 71 | not determined |
| 5'-T$_{10}$ | (E') | 24/20 | 18 |
| 5'-T$_{14}$ | (E) | 31 | 29 |

[a]X = monomer derived from phosphoramidite 11
[b]Complexed with 5'-dA$_{14}$
[c]Complexed with 5'-rA$_{14}$

TABLE 2

| Sequence[a] | | $T_m$ (° C.)[b] | $T_m$ (° C.)[c] |
|---|---|---|---|
| 5'-T$_7$YT$_6$ | (H) | 21 | 21 |
| 5'-T$_5$Y$_4$T$_5$ | (I) | no $T_m$ | no $T_m$ |
| 5'-T$_{14}$ | (E) | 31 | 29 |

[a]Y = monomer derived from phosphoramidite 21
[b]Complexed with 5'-dA$_{14}$
[c]Complexed with 5'-rA$_{14}$

The invention claimed is:

1. An oligomer comprising at least one nucleoside analogue (Xylo-LNA) of the general formula I

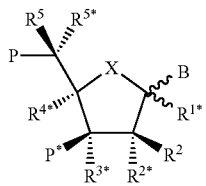

wherein X is —O—, and the sugar group of formula I is xylofuranosyl;

B is selected from hydrogen, hydroxy, optionally substituted C$_{1-4}$-alkoxy, optionally substituted C$_{1-4}$-alkyl, optionally substituted C$_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent R$^5$ or equally applicable the substituent R$^{5*}$;

P* designates an internucleoside linkage to a preceding monomer, or a 3'-terminal group;

R$^{2*}$ and R$^{4*}$ together designate a biradical consisting of 1–4 groups/atoms selected from —(CR*R*)$_r$—Y—(CR*R*)$_s$—, —(CR*R*)$_r$—Y—(CR*R*)$_s$—Y—, —Y—(CR*R*)$_{r+s}$—Y—, —Y—(CR*R*)$_r$—Y—(CR*R*)$_s$—, —(CR*R*)$_{r+s}$—, —Y—, —Y—Y—, wherein each Y is —O—, —S—, —N(R$^{N*}$)—, each R* is independently selected from hydrogen, halogen, hydroxy, mercapto, amino, optionally substituted C$_{1-6}$-alkoxy, optionally substituted C$_{1-6}$-alkyl, and/or two adjacent (non-geminal) R* may together designate a double bond, and each of r and s is 0–4 with the proviso that the sum r+s is 1–4, each of the substituents R$^{1*}$, R$^2$, R$^{3*}$, R$^5$, R$^{5*}$, which are present is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanolyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atoms(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present is selected from hydrogen and C$_{1-4}$-alkyl;

and basic salts and acid addition salts thereof.

2. An oligomer according to claim 1, comprising 1–10000 Xylo-LNA(s) of the general formula I and 0–10000 nucleosides selected from naturally occurring nucleosides and nucleoside analogues, with the proviso that the sum of the number of nucleosides and the number of Xylo-LNA(s) is in the range of 2–15000.

3. An oligomer according to claim 2, wherein at least one Xylo-LNA comprises a nucleobase as the substituent B.

4. An oligomer according to claim 1, wherein the Xylo-LNA(s) has/have the following formula 1a

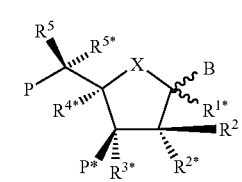

wherein P, P*, B, X, R1*, R2, R2*, R3*, R4*, R5, and R5* are as defined in claim 1.

5. An oligomer according to claim 1, wherein the biradical is selected from —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, wherein each of r and s is 0–3 with the proviso that the sum r+s is 1–4.

6. An oligomer according to claim 5, wherein the biradical is —O—CH$_2$—, —S—CH$_2$— or —N(R$^N$)—CH$_2$—.

7. An oligomer according to claim 1, wherein the oligomer comprises at least one Xylo-LNA wherein B is selected from adenine and guanine and at least one Xylo-LNA wherein B is selected from thymine, cytosine and uracil.

8. An oligomer according to claim 5, wherein the biradical is —(CH$_2$)$_{2-4}$—.

9. An oligomer according to any of the claims 6–8, wherein one R* is selected from hydrogen, hydroxy, optionally substituted C$_{1-6}$-alkoxy, optionally substituted C$_{1-6}$-alkyl, and any remaining substituents R* are hydrogen.

10. An oligomer according to claim 1, wherein any internucleoside linkage of the Xylo-LNA(s) is selected from linkages consisting of 3, groups/atoms selected from —CH$_2$—, —O—, —S—, —NR$^H$—, >C=O, >C=NR$^H$, >C=S, —Si(R")$_2$—, —SO—, —S(O)$_2$—, —P(O)$_2$—, —P(O,S)—, —P(S)$_2$—, —PO(R")—, —PO(OCH$_3$)—, and —PO(NHR$^H$)—, where R$^H$ is selected from hydrogen and C$_{1-4}$-alkyl, and R" is selected from C$_{1-6}$-alkyl and phenyl.

11. An oligomer according to claim 10, wherein any internucleoside linkage of the Xylo-LNA(s) is selected from —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH₂—CH=, —CH₂—CH₂—O—, NR^H—CH₂—CH₂—, —CH₂—CH₂—NR^H—, —CH₂—NR^H—CH₂—, —O—CH₂—CH₂—NR^H—, —NR^H—CO—O—, —NR^H—CO—NR^H—, —NR^H—CS—NR^H—, —NR^H—C(=NR^H)—NR^H—, —NR^H—CO—CH₂—NR^H—, —O—CO—O—, —O—CO—CH₂—O—, —O—CH₂—CO—O—, —CH₂—CO—NR^H—, —O—CO—NR^H—, —NR^H—CO—CH₂—, —O—CH₂—CO—NR^H—, —O—CH₂—CH₂—NR^H—, —CH=N—O—, —CH₂—NR^H—O—, —CH₂—O—N=, —CH₂—O—NR^H—, —CO—NR^H—CH₂—, —CH₂—NR^H—O—, —CH₂—NR^H—CO—, —O—NR^H—CH₂—, —O—NR^H—, —O—CH₂—S—, —S—CH₂—O—, —CH₂—CH₂—S—, —O—CH₂—CH₂—S—, —S—CH₂—CH=, —S—CH₂—CH₂—, —S—CH₂—CH₂—O, —S—CH₂—CH₂—S—, —CH₂—S—CH₂—, —CH₂—SO—CH₂—, —CH₂—SO₂—CH₂—, —O—SO—O—, —O—S(O)₂—O—, —O—S(O)₂—CH₂—, —O—S(O)₂—NR^H—, —NR^H—S(O)₂—CH₂—, —O—S(O)₂—CH₂—, —O—P(O)₂—O—, —O—P(O,S)—O—, —O—P(S)₂—O—, —S—P(O)₂—O—, —S—P(O,S)—O—, —S—P(S)₂—O—, —O—P(O)₂—S—, —O—P(O,S)—S—, —O—P(S)₂—S—, —S—P(O)₂—S—, —S—P(O,S)—S—, —S—P(S)₂—S—, —O—PO(R")—O—, —O—PO(OCH₃)—O—, —O—PO(BH₃)—O—, —O—PO(NHR^N)—O—, —O—P(O)₂—NR^H—, —NR^H—P(O)₂—O—, —O—P(O,NR^H)—O—, and —O—Si(R")₂—O—.

12. An oligomer according to claim 1, wherein each of the substituents R^{1*}, R^2, R^{3*}, R^5, R^{5*}, of the Xylo-LNA(s), which are present, designate hydrogen.

13. An oligomer according to claim 1, having the following formula V:

G-[Nu-L]_{n(0)}{[Xylo-LNA-L]_{m(q)}[NU-L]_{n(q)}}_q-G*    V wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each Xylo-LNA independently designates a nucleoside analogue;

each L independently designates an internucleoside linkage between two groups selected from Nu and Xylo-LNA, or L together with G* designates a 3'-terminal group; and each Xylo-LNA-L independently designates a nucleoside analogue of the general formula 1.

14. A nucleoside analogue (Xylo-LNA) of the general formula II

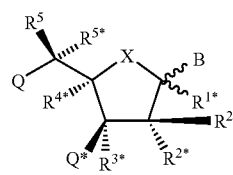

II wherein the substituent B is selected from nucleobases, DNA intercalators, photochemically active groups, thermochemically active groups, chelating groups, reporter groups, and ligands;

X is —O—;

each of Q and Q* is independently selected from hydrogen, azido, halogen, cyano, nitro, hydroxy, Prot-O—, Act-O—, mercapto, Prot-S, Act-S—, $C_{1-6}$-alkylthio, amino, Prot-N(R^H)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, disphosphate, triphosphate, DNA intercalators, photochemically active groups, thermochemically active groups, chelating groups, reporter groups, ligands, carboxy, sulphono, hydroxymethyl, Prot-O—CH₂, Act-O—CH₂—. aminomethyl, Prot-N(R^H)—CH₂—, Act-N(R^H)—CH₂—. carboxymethyl, sulphonomethyl, where Prot is a protection group for —OH, —SH, and —NH(R^H), respectively, Act is an activation group for —OH, —SH, and —NH(R^H), respectively, and R^H is selected from hydrogen and $C_{1-6}$-alkyl; and $R^{2*}$ and $R^{4*}$ together designate a biradical selected from —(CR*R*)_{r+s+1}—, —(CR*R*)_r—O—(CR*R*)_s—, —(CR*R*)_r—S—(CR*R*)_s—, —(CR*R*)_r—N(R*)—(CR*R*)_s—, —O—(CR*R*)_{r+s}—O—;

wherein each R* is independently selected from hydrogen, halogen, azido, hydroxy, mercapto, amino, optionally substituted $C_{1-6}$-alkoxy, optionally substituted $C_{1-6}$-alkyl, and/or two adjacent (non-geminal) R* may together designate a double bond, and each of r and s is 0–3 with the proviso that the sum r+s is 1–4;

each of the present substituents $R^{1*}$, $R^2$, $R^{3*}$, $R^5$, $R^{5*}$ is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a Spiro biradical consisting of a 1–5 carbon atom(s) alkylene chain which is optionally interrupted and/or terminated by one or more heteroatoms/groups selected from —O—, —S—, and —(NR^N)— where R^N is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof;

and with the proviso that any chemical group which is reactive under the conditions prevailing in oligonucleotide synthesis, is optionally functional group protected.

15. A nucleoside analogue according to claim 14, wherein the group B is selected from nucleobases and functional group protected nucleobases.

16. A nucleoside analogue according to claim 14, wherein each of the substituents $R^{1*}$, $R^2$, $R^{3*}$, $R^5$, $R^{5*}$, which are present, is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, ligands, and halogen, where two geminal substituents together may designate oxo, and where $R^{N*}$, when present and not involved in a biradical, is selected from hydrogen and $C_{1-4}$-alkyl, with the proviso that any hydroxy, amino, mono($C_{1-6}$-alkyl)amino, sulfanyl, and carboxy is optionally protected.

17. A nucleoside analogue according to claim 14, wherein each of the substituents $R^{1*}$, $R^2$, $R^{3*}$, $R^5$, $R^{5*}$, which are present, designate hydrogen.

18. A nucleoside analogue according to claim 14, wherein Q is independently selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, aminomethyl, Prot-N($R^H$)—CH$_2$—, carboxymethyl, sulphonomethyl, where Prot is a protection group for —OH—, —SH, and —NH($R^H$), respectively, and $R^H$ is selected from hydrogen and $C_{1-6}$-alkyl; and Q* is selected from hydrogen, azido, halogen, cyano, nitro, hydroxy, Act-O—, mercapto, Act-S—, $C_{1-6}$-alkylthio, amino, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, DNA intercalators, photochemically active groups, thermochemically active groups, chelating groups, reporter groups, ligands, carboxy, sulphono, where Act is an activation group for —OH, —SH, and —NH($R^H$), respectively, and $R^H$ is selected from hydrogen and $C_{1-6}$-alkyl.

19. A nucleoside analogue according to claim 14, wherein the biradical is —O—, and —(CH$_2$)$_{0-1}$—O—(CH$_2$)$_{1-3}$—.

20. A nucleoside analogue according to claim 14, wherein B is selected from adenine, guanine, thymine, cytosine and uracil.

21. The Xylo-LNA modified oligonucleotide as defined in claim 1 conjugated with a compound selected from the group consisting of proteins, amplicons, enzymes, polysaccharides, antibodies, haptens, peptides, and PNA.

22. A kit for the isolation, purification, amplification, detection, identification, quantification, or capture of natural or synthetic nucleic acids, the kit comprising a reaction body and one or more Xylo-LNA modified oligonucleotides as defined in claim 1.

23. A kit for the isolation, purification, amplification, detection, identification, quantification, or capture of natural or synthetic nucleic acids, the kit comprising a reaction body and one or more Xylo-LNA modified oligonucleotides as defined in claim 1.

24. A kit according to claim 22, wherein the Xylo-LNA modified oligonucleotides are immobilised onto said reaction body.

25. A kit for the isolation, purification, amplification, detection, identification, quantification, or capture of natural or synthetic nucleic acids, the kit comprising a reaction body and one or more Xylo-LNAs as defined in claim 14.

26. A kit according to claim 25, wherein the Xylo-LNAs are immobilised onto said reaction body.

27. A composition comprising one or more Xylo-LNA modified oligonucleotides of claim 1.

28. The Xylo-LNA modified oligonucleotide as defined in claim 1 further comprising a pharmaceutically acceptable carrier.

29. The oligomer of claim 1, wherein R1* is in a β configuration.

30. The nucleoside analogue of claim 14, wherein R1* is in a β configuration.

31. An oligomer comprising at least one nucleoside analogue (Xylo-LNA) of the general formula I

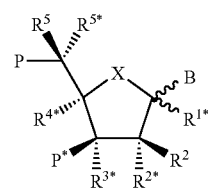

wherein X is —O— and the sugar group of formula I is xylofuranosyl;

B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{2*}$ and $R^{4*}$ together designate a biradical consisting of 1–4 groups/atoms selected from —C($R^a$)=C($R^a$)—, —C($R^a$)=N—, wherein $R^a$ is independently selected from hydrogen, hydroxyl, or lower alkyl, each of the substituents $R^{1*}$, $R^2$, $R^{3*}$, $R^5$, $R^{5*}$ which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanolyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atoms(s) alkylene chain which is optionally interrupted and/or terminated by one or more heteroatoms/groups selected from —O—, —S—, and —(NR$^N$)— where R$^N$ is selected from hydrogen and $C_{1-4}$-alkyl, and where two adjacent (non-geminal) substituents may designate an additional bond resulting in a double bond; and R$^{N*}$, when present is selected from hydrogen and $C_{1-4}$-alkyl;

and basic salts and acid addition salts thereof.

32. The nucleoside analogue (Xylo-LNA) of claim 14, wherein Q* represents an activation group for —OH, —SH, and —NH(R$^H$).

33. The nucleoside analogue (Xylo-LNA) of claim 32, wherein said activation group is an optionally substituted O-phosphoramidite.

34. The nucleoside analogue (Xylo-LNA) of claim 14, wherein the nucleoside analogue is a 3'-phosphoramidite derivative.

35. The nucleoside analogue (Xylo-LNA) of claim 33, wherein said O-phosphoramidite is a N,N-diisopropyl-O-(2-cyanoethyl)phosphoramidite.

36. A nucleoside analogue (Xylo-LNA) having the following general formula:

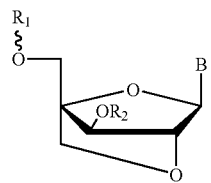

wherein the substituent B is a nucleobase, $R_1$ is a hydroxy protecting group; and $R_2$ is a phosphoramidite.

37. The nucleoside analogue (Xylo-LNA) of claim 36, wherein $R_1$ is dimethoxytrityl (DMT) and $R_2$ is —P(N(iPr)$_2$)(O(CH$_2$)$_2$CN.

38. An oligomer comprising at least one nucleoside analogue (Xylo-LNA) having the following general formula:

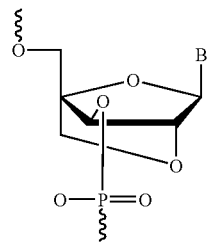

wherein the substituent B is a nucleobase.

39. A kit for the isolation, purification, amplification, detection, identification, quantification, or capture of natural or synthetic nucleic acids, the kit comprising a reaction body and one or more Xylo-LNA modified oligonucleotides as defined in claim 38.

40. A composition comprising one or more Xylo-LNA modified oligonucleotides of claim 38.

41. The Xylo-LNA modified oligonucleotide as defined in claim 38 further comprising a pharmaceutically acceptable carrier.

* * * * *